(12) United States Patent
Hutchinson et al.

(10) Patent No.: US 10,752,490 B2
(45) Date of Patent: *Aug. 25, 2020

(54) AUTOMATED WATER AND PARTICLE DETECTION FOR DISPENSING FUEL INCLUDING AVIATION FUEL

(71) Applicants: Ray Hutchinson, Houma, LA (US); John Joseph Hutchinson, Spring, TX (US)

(72) Inventors: Ray Hutchinson, Houma, LA (US); John Joseph Hutchinson, Spring, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/456,425

(22) Filed: Jun. 28, 2019

(65) Prior Publication Data
US 2019/0322519 A1 Oct. 24, 2019

Related U.S. Application Data

(63) Continuation of application No. 15/010,031, filed on Jan. 29, 2016, now Pat. No. 10,364,139.

(60) Provisional application No. 62/109,429, filed on Jan. 29, 2015.

(51) Int. Cl.
| | |
|---|---|
| *B67D 7/06* | (2010.01) |
| *G01N 33/22* | (2006.01) |
| *B67D 7/04* | (2010.01) |
| *B64F 1/28* | (2006.01) |

(52) U.S. Cl.
CPC ............... *B67D 7/06* (2013.01); *B67D 7/04* (2013.01); *G01N 33/22* (2013.01); *B64F 1/28* (2013.01)

(58) Field of Classification Search
None
See application file for complete search history.

(56) References Cited

U.S. PATENT DOCUMENTS

| | | |
|---|---|---|
| 3,221,248 A | 11/1965 | Batteau et al. |
| 3,748,576 A | 7/1973 | Sigoumay |
| 3,771,624 A | 11/1973 | Forgeron |
| 3,824,823 A | 7/1974 | Pontello |
| 3,876,307 A | 4/1975 | Skala |
| 4,721,563 A | 1/1988 | Rosaen |
| 4,723,049 A | 2/1988 | Menard et al. |
| 4,814,087 A | 3/1989 | Taylor |
| 4,934,565 A | 6/1990 | Heisey et al. |

(Continued)

FOREIGN PATENT DOCUMENTS

| | | |
|---|---|---|
| AU | 2008206281 B2 | 7/2008 |
| EP | 0440299 A1 | 8/1991 |

(Continued)

OTHER PUBLICATIONS

Author Unknown, "AFGUARD—Prototype Quality Guarantees Safety," Jul. 9, 2006, 17 pages.

(Continued)

*Primary Examiner* — Harshad R Patel
(74) *Attorney, Agent, or Firm* — Withrow & Terranova, PLLC

(57) ABSTRACT

A fuel dispensing apparatus and method for delivering fuel from a fuel source is disclosed. The fuel dispensing apparatus also includes an electronic control system in communication with a particle detector. The electronic control system is configured to determine, based on raw particle counts of the particle detector, a particle ratio and whether the particle ratio exceeds a particle threshold.

22 Claims, 13 Drawing Sheets

(56) References Cited

U.S. PATENT DOCUMENTS

| | | | |
|---|---|---|---|
| 4,981,272 | A | 1/1991 | Cutore |
| 5,200,064 | A | 4/1993 | Russ et al. |
| 5,268,095 | A | 12/1993 | Barzuza |
| 5,437,256 | A | 8/1995 | Woletz et al. |
| 5,455,513 | A | 10/1995 | Brown et al. |
| 5,534,708 | A | 7/1996 | Ellinger et al. |
| 5,711,456 | A | 1/1998 | Bryant |
| 5,719,781 | A | 2/1998 | Leatherman et al. |
| 5,720,176 | A | 2/1998 | Manson et al. |
| 5,722,469 | A | 3/1998 | Tuminaro |
| 5,754,055 | A | 5/1998 | McAdoo et al. |
| 5,784,742 | A | 7/1998 | Giuliani et al. |
| 5,794,667 | A | 8/1998 | Payne et al. |
| 5,880,480 | A | 3/1999 | Ellinger et al. |
| 5,971,042 | A | 10/1999 | Hartsell, Jr. |
| 6,121,628 | A | 9/2000 | Rising |
| 6,126,818 | A | 10/2000 | Duerrstein et al. |
| 6,163,738 | A | 12/2000 | Miller |
| 6,182,710 | B1 | 2/2001 | Webb |
| 6,223,765 | B1 | 5/2001 | Small et al. |
| 6,361,684 | B1 | 3/2002 | Hawkins et al. |
| 6,470,233 | B1 | 10/2002 | Johnson, Jr. |
| 6,803,775 | B2 | 10/2004 | Sanchez et al. |
| 6,926,827 | B2 | 8/2005 | Gruca et al. |
| 6,935,191 | B2 | 8/2005 | Olivier et al. |
| 6,992,569 | B2 | 1/2006 | Nimberger et al. |
| 6,996,970 | B2 | 2/2006 | Lorenz |
| 7,174,273 | B2 | 2/2007 | Goldberg |
| 7,412,896 | B2 | 8/2008 | Janik et al. |
| 7,518,719 | B2 | 4/2009 | Sprenger et al. |
| 7,765,978 | B2 | 8/2010 | Ruesch et al. |
| 8,149,401 | B2 | 4/2012 | Stevens et al. |
| 8,720,499 | B2 | 5/2014 | Kastner et al. |
| 9,530,290 | B2 | 12/2016 | Hutchinson |
| 2004/0232075 | A1 | 11/2004 | Wells |
| 2005/0040834 | A1 | 2/2005 | Sanchez et al. |
| 2005/0092074 | A1 | 5/2005 | Beaucaire et al. |
| 2005/0150304 | A1 | 7/2005 | Gustafson et al. |
| 2005/0242110 | A1 | 11/2005 | Waugh et al. |
| 2007/0044865 | A1 | 3/2007 | Ruesch et al. |
| 2007/0119859 | A1 | 3/2007 | Harrell |
| 2008/0230146 | A1 | 9/2008 | Kastner et al. |
| 2014/0202580 | A1 | 7/2014 | Hutchinson |
| 2014/0226149 | A1 | 8/2014 | Coates et al. |

FOREIGN PATENT DOCUMENTS

| | | |
|---|---|---|
| EP | 2122325 B1 | 3/2013 |
| WO | 2008089259 A2 | 7/2008 |
| WO | 2010013084 A1 | 2/2010 |

OTHER PUBLICATIONS

Author Unknown, "Aviation," Facet, a Clarcor company, Dec. 13, 2006, accessed Apr. 19, 2012, 2 pages, hittp://www.facetusa.com/f_aviation_index.htm.

Author Unknown, "D-2 Incorporated Announces the Introduction of the Monitor/Filter Condition Sensor, JF-M3," D2 Incorporated, Jan. 23, 2007, 4 pages.

Author Unknown, "EZ-LIGHT™ Indicators—Daylight Visible," P/N 137330 rev. B, Mar. 22, 2011, Banner Engineering Corportation, http://info.bannerengineering.com/cs/groups/public/documents/literature/137330.pdf, 4 pages.

Author Unknown, "Gammon Gauge", Bulletin 25, Gammon Technical Products, Inc., Jul. 2005, 4 pages, http://www.gammontech.com/mainframe/pdf/b025.pdf.

Author Unknown, "HIAC PM4000: On-Line Liquid Particle Monitors," Hach Lange, 2007, http://www.hach-lange.ma/countrysites/action_q/download%3Bdocument/DOK_ID/14787582/type/pdf/Ikz/MA/spkz/fr/TOKEN/1Qla0rKzGuYbDYf6lujfZQ6rDal/M/Tt4IWA, 2 pages.

Author Unknown, "MS100 Moisture Sensor," Hydraulic Filtration and Contamination Control: Solutions for Industry, Catalogue FDHB200UK, Section 40, Nov. 2007, Parker Hannifin Corporation, pp. 262-265.

Author Unknown, "Operator Manual: HIAC PM400 On-line Laser Particle Monitor," Hach Ultra, Edition 5, Dec. 6, 2007, http://www.atotest.com.tr/download/kilavuz/PM4000kilavuzEN.pdf, 90 pages.

Author Unknown, "Quantum 4" Submersible Pumps: Installation, Operation, Service & Repair Parts," Part No. 042-129-1 Rev. E, Veeder Root, Jun. 2001, 33 pages, http://www.veeder.com/object/042-129-1.html.

Examiner's First Report for Australian Patent Application No. 2008206281, dated May 31, 2012, 4 pages.

International Search Report for PCT/US 08/51197, dated Jul. 8, 2008, 3 pages.

International Preliminary Report on Patentability and Written Opinion for PCT/US2008/051197, dated Jul. 21, 2009, 8 pages.

Extended European Search Report and Supplementary European Search Report for PCT/US2008051197 (European Application No. 08727755.4), dated Jan. 4, 2012, 8 pages.

Decision to Grant for European Patent Application No. 08727755.4, dated Feb. 28, 2013, 3 pages.

Non-Final Office Action for U.S. Appl. No. 14/160,149, dated Feb. 25, 2016, 5 pages.

Non-Final Office Action for U.S. Appl. No. 12/015,111, dated Jul. 12, 2011, 17 pages.

Non-Final Office Action for U.S. Appl. No. 12/015,111, dated Mar. 15, 2012, 16 pages.

Final Office Action for U.S. Appl. No. 12/015,111, dated Nov. 21, 2012, 16 pages.

Non-Final Office Action for U.S. Appl. No. 12/015,111, dated Jun. 4, 2013, 17 pages.

Non-Final Office Action for U.S. Appl. No. 14/245,476 dated Mar. 13, 2015, 7 pages.

Notice of Allowance for U.S. Appl. No. 14,245,476, dated Aug. 20, 2015, 7 pages.

Notice of Allowance and Examiner-Initiated Interview Summary for U.S. Appl. No. 12/015,111, dated Dec. 20, 2013, 9 pages.

Author Unknown, "New revisions to IP 565 for Particle Counting in Jet Fuels improve accuracy," Apr. 24, 2013, SetaAnalytics, 6 pages.

Author Unknown, "Fuel Condition Monitoring & Control," 2014, Velcon Filtration Division, Parker Hannifin Corporation, 24 pages.

Schmitigal, Joel, "Evaluation of Particle Counter Technology for Detection of Fuel Contamination Detection utilizing Fuel System Supply Point," Technical Report, Jun. 2014, US Army TARDEC, 17 pages.

Extended European Search Report for European Patent Application No. 16153062.1, dated Jun. 15, 2016, 9 pages.

Examination Report for European Patent Application No. 16153062.1, dated Jul. 26, 2017, 4 pages.

Notice of Allowance for U.S. Appl. No. 14/160,149, dated Aug. 24, 2016, 14 pages.

Non-Final Office Action for U.S. Appl. No. 15/010,031, dated Feb. 15, 2018, 22 pages.

Final Office Action for U.S. Appl. No. 15/010,031, dated Sep. 6, 2018, 23 pages.

Applicant-Initiated Interview Summary for U.S. Appl. No. 15/010,031, dated Oct. 17, 2018, 4 pages.

Advisory Action and Examiner-Initiated Interview Summary for U.S. Appl. No. 15/010,031, dated Dec. 28, 2018, 5 pages.

Notice of Allowance for U.S. Appl. No. 15/010,031, dated Mar. 14, 2019, 6 pages.

Extended European Search Report for European Patent Application No. 19185725.9, dated Dec. 18, 2019, 6 pages.

AUTOMATED WATER AND PARTICLE DETECTION FOR DISPENSING FUEL INCLUDING AVIATION FUEL

PRIORITY APPLICATIONS

The present application claims priority to U.S. patent application Ser. No. 15/010,031 filed on Jan. 29, 2016 entitled "AUTOMATED WATER AND PARTICLE DETECTION FOR DISPENSING FUEL INCLUDING AVIATION FUEL, AND RELATED APPARATUSES, SYSTEMS, AND METHODS," now issued as U.S. Pat. No. 10,364,139, which in turn claims priority to U.S. Provisional Patent Application No. 62/109,429 filed on Jan. 29, 2015 entitled "AUTOMATED WATER AND PARTICLE DETECTION FOR DISPENSING FUEL INCLUDING AVIATION FUEL, AND RELATED APPARATUSES, SYSTEMS, AND METHODS," both of which are incorporated herein by reference in their respective entireties.

BACKGROUND

Field of the Disclosure

The field of the disclosure relates to automated water and particle detection for dispending fuel, including aircraft fuel, and related apparatuses, systems and methods; wherein the quality of fuel or supporting fueling components is monitored using sensing devices, either individually or in combination, to ensure that the fuel quality is acceptable to be dispensed for use.

Technical Background

Fuel dispensers are used to dispense fuel to vehicles and other equipment requiring fuel for operation. The basic components of a fuel dispenser are as follows. The fuel dispenser contains a fuel conduit that receives fuel from a fuel source and directs the received fuel to an outlet to be dispensed into a fuel holding tank of desired equipment when the fuel dispenser is activated. A pump, either self-contained within the fuel dispenser or located outside the fuel dispenser but coupled to the fuel conduit, provides the pumping force to direct the fuel through the fuel dispenser when activated. Once the fuel is pumped into the fuel conduit inside the fuel dispenser, the fuel encounters a number of fuel handling components located inline the fuel conduit before eventually being delivered. For example, the fuel encounters a meter to measure the amount of fuel being dispensed. A fuel flow control valve is located inline the fuel conduit, either on the inlet or outlet side of the meter, to control whether the fuel is allowed to pass through the fuel conduit to the outlet of the fuel dispenser. The outlet of the fuel dispenser is typically comprised of a flexible hose that is coupled to the fuel conduit on one end and to a nozzle on the other. A user engages the nozzle handle trigger to allow fuel flow. The nozzle contains its own fuel flow control valve that is trigger-activated by the user to control the dispensing of fuel.

An example of a fuel dispenser that is employed in the aviation industry, in particular to fuel aircraft, is illustrated in FIGS. 1A and 1B. As shown therein, a refueling truck 10 is provided that contains an onboard fuel tank 12 and an onboard fuel dispenser 14. The refueling truck 10 is mobile so that the onboard fuel dispenser 14 can be conveniently located proximate the desired aircraft for refueling the aircraft. Thus, the fuel tank 12 is located onboard. This is different from typical automobile fuel dispensers that are static and are not transported on trucks or other vehicles. As a result, fuel tanks 12 used to provide fuel to automobile fuel dispensers are located separate from the fuel dispenser, typically beneath the ground. An example of a typical automobile fuel dispenser is described in U.S. Pat. Nos. 5,719,781 and 6,470,233, incorporated by reference herein in their entirety. However, a typical automobile fuel dispenser contains similar components and performs similar functionalities to an aircraft refueling truck 10 with an onboard fuel dispenser 14.

As shown in the close-up illustration of the fuel dispenser 14 in FIG. 1B, a meter 16 is coupled inline the fuel conduit 18 to measure the fuel as it is delivered. A registration device or computer 20 is coupled to the meter 16 that converts the amount of fuel delivered through the meter 16 into a volumetric measurement, typically in the form of gallons. The computer 20 may also further convert the volumetric measurement into a price charged to the user for the fuel. The computer 20 typically contains a display that displays the volume of fuel dispensed, and price if applicable. After the fuel exits the meter 16 through the fuel conduit 18, the fuel is delivered to a hose 22 coupled to the fuel conduit 18. The user unwinds the hose 22, which is coiled in the example of the refueling truck 10 illustrated, and places the nozzle (not shown) coupled to the end of the hose 22 to the aircraft (not shown) desired to be refueled.

Debris/particulates and undissolved or free water can collect inside the fuel tank 12. Debris may be present due to debris being passed into the fuel tank 12 when fuel tank 12 is filled. Debris may also be present by rust or others failures of the material used to construct the inside of the fuel tank 12. Free water may also collect inside the fuel tank 12 as a result of condensation, or free water may be delivered with fuel as the tank is refilled. Both debris and free water in fuel can be hazardous to a vehicle and especially aircraft, because it may cause the engine to be disrupted and/or not perform in a safe manner. For this reason, it is important to prevent debris and free water from being dispensed into a vehicle or aircraft fuel tank that will reach its engine. Manual inspection tests, free water tests, and particle contaminant tests are employed to inspect fuel quality periodically by refueling personnel. For example, some fuel is dispensed into a jar or clear container called a "sight jar" that is typically mounted on the refueling truck 10 to visually inspect the fuel for impurities. Manual free water and particle tests may also be employed to detect the presence of water and/or particulate. However, these tests are subjective and subject to human error. Further, the test results are typically logged in a log book, thereby increasing the possibility for error due to the human factor. Log books can also be disputed.

As a result, filters are employed as an automatic method to prevent debris and water from passing through to the aircraft. Examples of fueling filters are the filter water separator and monitor filter manufactured by Facet, Velcon, or Faudi described at www.pecofacet.com/Markets/Aviation, which is incorporated herein by reference in its entirety. The filter is coupled inline the fuel conduit 18. Many filters not only collect debris, but also contain an absorbent material that collects water present in the fuel. However, filters can clog. Filters can clog by collecting and blocking debris or free water which closes off the size of the fuel flow path internal to the filter. As a result, the pressure differential across the filter increases. If the pressure goes too high, such as fifteen (15) pounds per square inch (p.s.i.) for example, the filter itself may break down causing debris to be passed on in the fuel to the vehicle or aircraft. Thus, a differential pressure sensor is often further employed to measure the pressure increase across the filter to indicate that the filter is clogged or may not be working properly. An increase in pressure beyond a certain threshold is indicative of a blockage. The filter can then be manually changed with a new, unclogged filter as a result.

One example of such a filter that employs a differential pressure monitor is the differential pressure filter gauge manufactured by Gammon, described at www.gammontech.com/mainframe/pdf/b025.pdf, which is incorporated herein by reference in its entirety. The filter apparatus contains a steel ball that is visible to refueling personnel and which floats higher in proportion to higher pressure across the filter. If the float reaches a level that indicates too high of a differential pressure across the filter, such as fifteen (15) p.s.i. for example, the refueling personnel interlocks the fuel conduit 18 and replaces the filter. Refueling personnel often attempt to continue refueling without replacing the filter, for example when the differential pressure reads twelve (12) p.s.i., as a result of the refueling personnel slowing the flow rate. This decreases the pressure across the filter thus making it less likely the filter will break down. Alternatively, refueling personnel may prematurely replace the filter when the differential pressure is not high enough to warrant such action, thereby increasing downtime and operation costs.

As a result, these manual tests are subject to human error, subjective decision making, non-guaranteed execution, and further may be performed prior to or after bad refueling conditions have taken place. In addition, the methods either rely on refueling personnel to replace filters on a predetermined maintenance schedule, or if a system is employed to shut down the truck when the differential pressure across the filter exceeds the safe level automatically, fuel flow is ceased abruptly and without warning, thus additionally inconveniencing the refueling personnel and the aircraft expecting to be refueled. Refueling personnel also make subjective decisions to slow flow rate based on a visual inspection of the differential pressure across the filter to lessen the likelihood of a filter break down. As a result, the fuel quality of fuel delivered may be inconsistent, and throughput efficiency may be reduced, by not replacing the filter in a timely and predicted manner.

SUMMARY

Embodiments disclosed herein include automated water and particle detection for dispensing fuel, including, without limitation, delivering aircraft fuel from a fuel tank to an aircraft. Related apparatuses, systems, and methods are also disclosed. In one example, the fuel dispensing apparatus includes a flow conduit defining a fluid flow path from a fuel source to an outlet where fuel is dispensed. A particle detector is provided in the flow conduit and configured to detect at least one fuel quality characteristic in real time as the fuel passes through the flow conduit. The fuel dispensing apparatus also includes an electronic control system in communication with the particle detector. The electronic control system is configured to receive fuel quality sensor information corresponding to the at least one detected fuel quality characteristic in real time. The electronic control system is further configured to determine, based on the received fuel quality sensor information, a particle ratio defined as an approximate ratio of a total measurement of water and particulate per unit volume of fuel. For example, without limitation, a particle ratio may be expressed as a total mass of particulate and/or water per unit of fuel in milligrams per Liter (mg/L), or may, alternatively, be expressed as a total volume of particulate and/or water per unit volume of fuel in parts-per-million (PPM). The electronic control system is further configured to determine, based on the received fuel quality sensor information, a first water characteristic indicative of the presence or absence of a threshold measurement of water per unit volume of fuel, such as, without limitation, the presence or absence of a volume of water above a predetermined PPM threshold. Further, some embodiments only require a single particle monitor to determine whether the fuel contains unacceptable levels of particulate and/or free water.

Based on the first water characteristic and on the particle ratio, the electronic control system is further configured to determine whether to initiate at least one corrective action, and to automatically initiate the at least one corrective action in response to this determination. For example, without limitation, if the first water characteristic indicates the absence of the threshold amount of water per unit volume of fuel, and if the particle ratio exceeds a first fuel quality threshold, the electronic control system may automatically direct the fuel dispensing apparatus to take a first corrective action, such as, without limitation, setting an alarm condition, or reducing or preventing a flow of fuel through the fluid flow path. In another example, if the first water characteristic indicates the presence of a threshold amount of water per unit volume of fuel, and if the particle ratio exceeds a second fuel quality threshold, which may be the same as or different than the first fuel quality threshold, the electronic control system may automatically direct the fuel dispending apparatus to take a second corrective action, which may be the same as or different from the first correction action.

One advantage of the above arrangement is that fuel quality can be monitored in real time, and with a high degree of accuracy. By identifying the presence of contamination from particulate and/or free water in fuel in real time as the fuel is being delivered, corrective action can be taken before unacceptable levels of contamination have been delivered to a fuel receptacle. In some embodiments, the above arrangement can also detect the presence of contamination from particulate and/or free water in fuel in concentrations lower than what is currently required by government agencies, such as the ATA 103 Standard used by the Federal Aviation Administration (FAA). One advantage of embodiments that only require one sensor to detect both particulate and free water is a significant reduction in cost and complexity of the fuel dispenser over existing arrangements.

In one exemplary embodiment, a fuel dispensing apparatus for delivering fuel from a fuel source is disclosed. The fuel dispensing apparatus comprises a flow conduit defining a fluid flow path from a fuel source to an outlet where fuel is dispensed, a particle detector configured to detect at least one fuel quality characteristic in real time as the fuel passes through the flow conduit, and an electronic control system in communication with the particle detector and configured to receive fuel quality sensor information corresponding to the at least one detected fuel quality characteristic in real time. The electronic control system is further configured to determine, based on the received fuel quality sensor information, a particle ratio defined as an approximate ratio of a total measurement of water and particulate per unit volume of fuel. The electronic control system is further configured to determine, based on the received fuel quality sensor information, a first water characteristic indicative of the presence or absence of a threshold measurement of water per unit volume of fuel. The electronic control system is further configured to determine, based on the first water characteristic and on the particle ratio, whether to initiate at least one corrective action. The electronic control system is further configured to automatically initiate the at least one corrective action in response to a determination to initiate the at least one corrective action.

In another exemplary embodiment a method of dispensing fuel is disclosed. The method comprises detecting, at a particle sensor, at least one fuel quality characteristic in real time as fuel passes through a flow conduit. The method further comprises receiving, at an electronic control system, fuel quality sensor information corresponding to the at least one detected fuel quality characteristic in real time. The method further comprises determining, at the electronic control system, based on the received fuel quality sensor information, a particle ratio defined as an approximate ratio of a total measurement of water and particulate per unit volume of fuel. The method further comprises determining, at the electronic control system, based on the received fuel quality sensor information, a first water characteristic indicative of the presence or absence of a threshold measurement of water per unit volume of fuel. The method further comprises determining, at the electronic control system, based on the first water characteristic and on the particle ratio, whether to initiate at least one corrective action. The method further comprises automatically initiating the at least one corrective action in response to a determination to initiate the at least one corrective action.

Those skilled in the art will appreciate the scope of the present invention and realize additional aspects thereof after reading the following detailed description of the preferred embodiments in association with the accompanying drawing figures.

BRIEF DESCRIPTION OF THE FIGURES

The accompanying drawing figures incorporated in and forming a part of this specification illustrate several aspects of embodiments disclosed herein, and together with the description serve to explain the principles of embodiments disclosed herein.

DETAILED DESCRIPTION

Figure 1A:
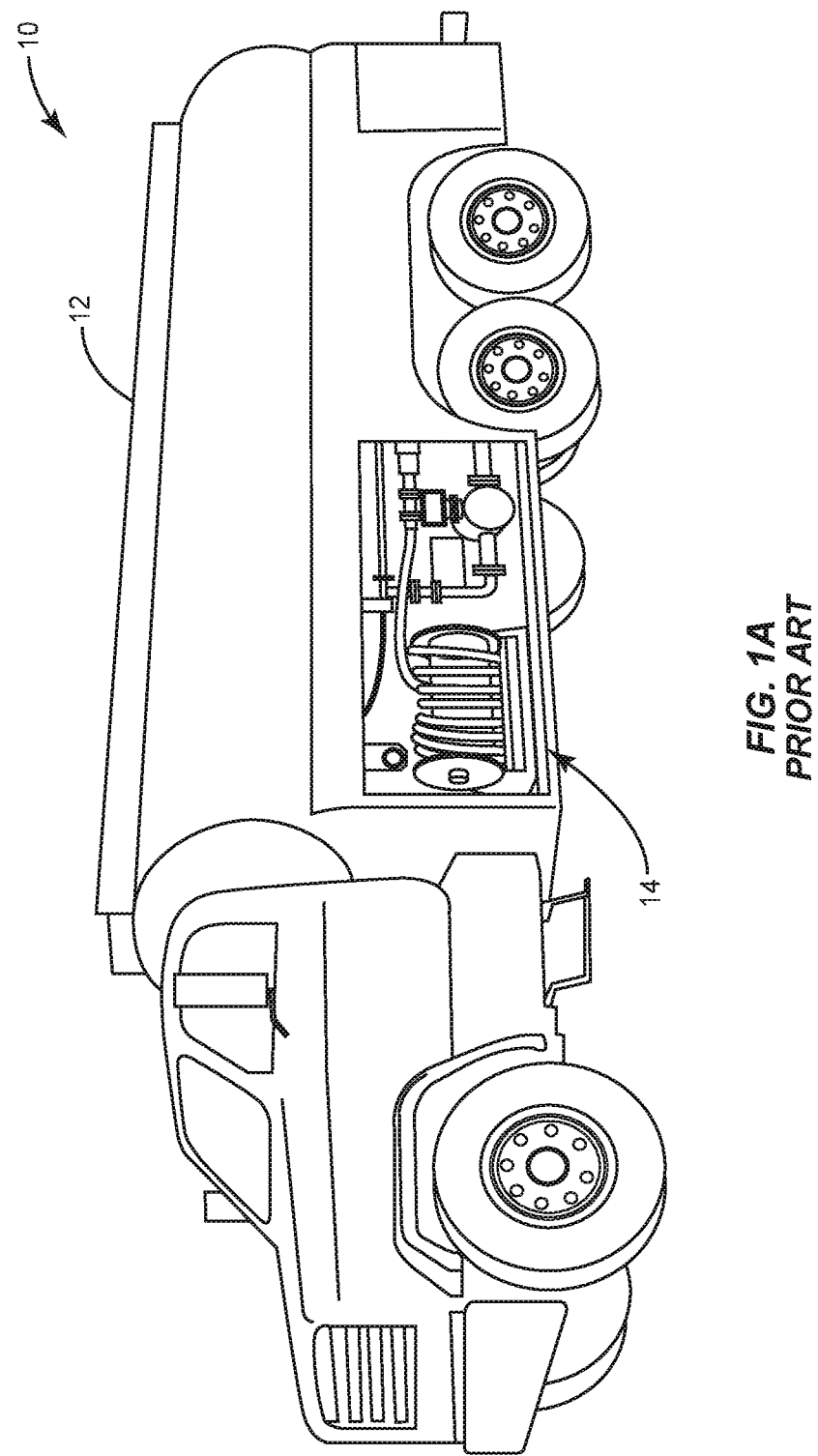
FIGS. 1A and 1B are schematic diagrams of a fueling truck and a fuel dispenser onboard the fueling truck in the prior art used to dispense fuel into aircraft.
Figure 1B:
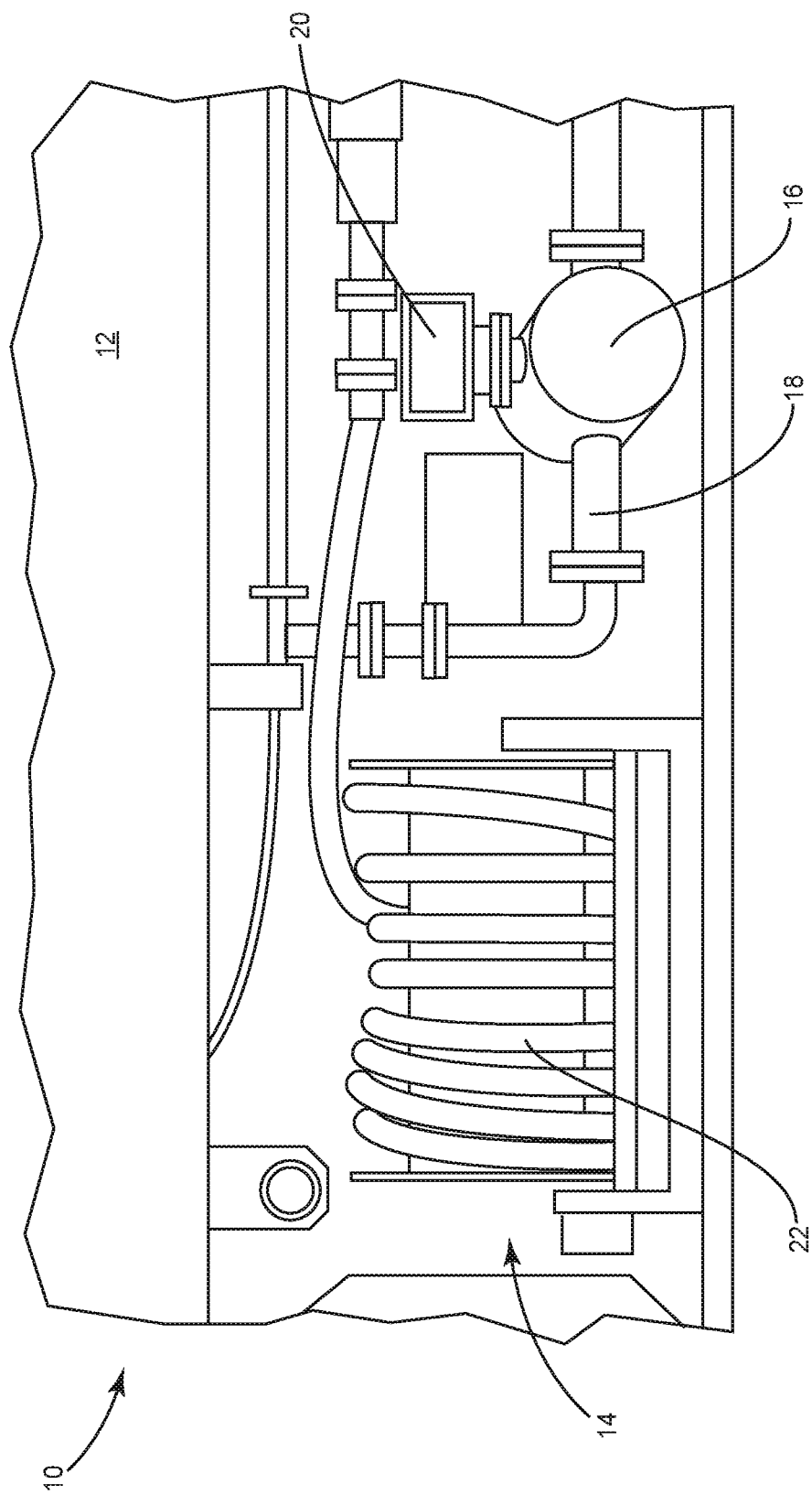

Embodiments disclosed herein include automated free water and particle detection for dispensing fuel, including, without limitation, delivering aircraft fuel from a fuel tank to an aircraft. Related apparatuses, systems, and methods are also disclosed. In one example, the fuel dispensing apparatus includes a flow conduit defining a fluid flow path from a fuel source to an outlet where fuel is dispensed. A particle detector is provided in the flow conduit and configured to detect at least one fuel quality characteristic in real time as the fuel passes through the flow conduit. The fuel dispensing apparatus also includes an electronic control system in communication with the particle detector. The electronic control system is configured to receive fuel quality sensor information corresponding to the at least one detected fuel quality characteristic in real time. The electronic control system is further configured to determine, based on the received fuel quality sensor information, a particle ratio defined as an approximate ratio of a total measurement of water and particulate per unit volume of fuel. For example, without limitation, a particle ratio may be expressed as a total mass of particulate and/or water per unit of fuel in milligrams per Liter (mg/L), or may, alternatively, be expressed as a total volume of particulate and/or water per unit volume of fuel in parts-per-million (PPM). The electronic control system is further configured to determine, based on the received fuel quality sensor information, a first water characteristic indicative of the presence or absence of a threshold measurement of water per unit volume of fuel, such as, without limitation, the presence or absence of a volume of water above a predetermined PPM threshold. Further, some embodiments only require a single particle monitor to determine whether the fuel contains unacceptable levels of particulate and/or free water.

Based on the first water characteristic and on the particle ratio, the electronic control system is further configured to determine whether to initiate at least one corrective action, and to automatically initiate the at least one corrective action in response to this determination. For example, without limitation, if the first water characteristic indicates the absence of the threshold amount of water per unit volume of fuel, and if the particle ratio exceeds a first fuel quality threshold, the electronic control system may automatically direct the fuel dispensing apparatus to take a first corrective action, such as, without limitation, setting an alarm condition, or reducing or preventing a flow of fuel through the fluid flow path. In another example, if the first water characteristic indicates the presence of a threshold amount of water per unit volume of fuel, and if the particle ratio exceeds a second fuel quality threshold, which may be the same as or different than the first fuel quality threshold, the electronic control system may automatically direct the fuel dispending apparatus to take a second corrective action, which may be the same as or different from the first correction action.

One advantage of the above arrangement is that fuel quality can be monitored in real time, and with a high degree of accuracy. By identifying the presence of contamination from particulate and/or free water in fuel in real time as the fuel is being delivered, corrective action can be taken before unacceptable levels of contamination have been delivered to a fuel receptacle. In some embodiments, the above arrangement can also detect the presence of contamination from particulate and/or free water in fuel in concentrations lower than what is currently required by government agencies, such as the ATA 103 Standard used by the Federal Aviation Administration (FAA). One advantage of embodiments that only require one sensor to detect both particulate and free water is a significant reduction in cost and complexity of the fuel dispenser over existing arrangements.

Figure 2:
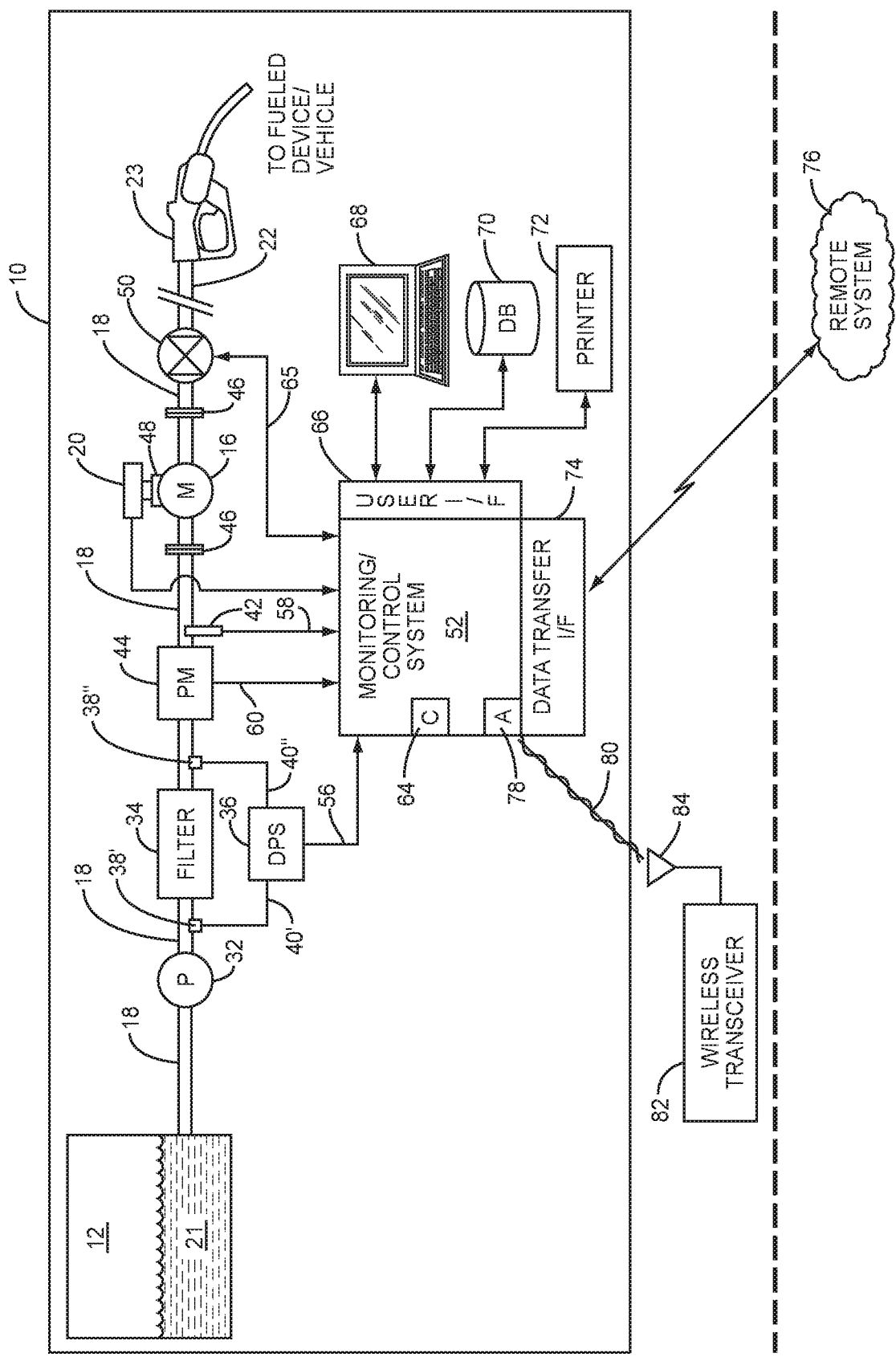
FIG. 2 is a schematic diagram of a quality detection and prevention monitoring and control system according to one embodiment that may be employed on the fueling truck illustrated in FIGS. 1A and 1B to monitor the quality of fuel or supporting fueling components in the fuel delivery flow path.

Before discussing the particular aspects of the apparatuses and methods for using particle count to identify and/or quantify particulate and free water contamination in fuels including but not limited to transportation, aviation, and industrial fuels, an exemplary architecture of a fuel dispenser 14 in accordance with one embodiment is illustrated in FIG. 2 and described below. Turning to FIG. 2, element 10 is intended to represent the refueling truck 10 since the disclosed exemplary embodiment is a fuel dispenser for aviation applications. However, this embodiment may be employed in any type of fuel dispenser for any application desired. The refueling truck 10 contains its own fuel tank 12 that contains fuel 21 to be dispensed. A fuel conduit 18 is coupled to the fuel tank 12 to receive fuel 21 when dispensing is desired.

A moisture and free water sensor 42, or other water detector, allows a control system 52 to determine if a fuel filter 34 is properly removing or absorbing water, as will be described later below.

A pump 32 is provided on the outlet side of a sump that pumps the fuel 21 from the fuel tank 12 into the fuel conduit 18 and towards a nozzle 23 for dispensing. The pump 32 can be any type of pump, including a vacuum or pressure based pump, and/or a mechanical or electro-mechanical pump, including a turbine pump and/or Venturi-based pump. For aviation fueling applications, the pump 32 is onboard the refueling truck 10. For vehicle fueling applications, the pump 32 may be inside the fuel dispenser or may be located proximate the fuel storage tank underneath the ground in the form of a submersible turbine pump. An example of a submersible turbine pump manufactured by Veeder-Root Company is the Quantum submersible turbine pump disclosed at www.veeder.com/page/PumpManuals, Quantum 4" Submersible Pumps Installation, Operation, Service & Repair Parts (042-129-1 Rev E) (PDF), and the pump described in U.S. Pat. No. 6,223,765, both of which are incorporated herein by reference in their entireties.

After the fuel 21 leaves the pump 32, the fuel 21 enters the fuel filter 34, which filters any debris and/or free water. The fuel filter 34 may be may be the Filter Water Separator or Filter Monitor filter, disclosed at www.facetusa.com/f_aviation_index.htm, incorporated herein by reference in its entirety. The fuel filter 34 collects any debris or free water that is present in the fuel 21. The fuel filter 34 may contain a water absorbent material, as in a Filter Monitor filter, that decreases the internal fuel flow path (not shown) in the fuel filter 34, thereby causing an increased pressure drop across the fuel filter 34. Debris collected by the fuel filter 34 also causes the pressure drop across the fuel filter 34 to increase. Fuel 21 passes through the fuel filter 34 without obstruction unless debris or free water has been collected and is being retained in the fuel filter 34. The fuel filter 34 is a replaceable device that is exchanged for a clean, unclogged filter periodically so that the fuel filter 34 will continue to operate to separate and prevent debris and free water from passing through a hose 22 to reach the nozzle 23 and being dispensed with the fuel 21.

The fuel filter 34 is also typically designed to accommodate up to a threshold pressure, e.g., 15 p.s.i., in the internal fuel flow path (not shown) before the elements of the fuel filter 34 are at risk of beginning to break down and block or clog the fuel filter 34. The fuel filter 34 will break down over time due to wear, which will cause its differential pressure to decrease when the fuel filter 34 has broken down or failed. In order to detect the differential pressure across the fuel filter 34, a differential pressure sensor 36 may be employed, as illustrated in FIG. 2. The differential pressure sensor 36 senses the pressure drop across the inlet 38' and outlet side 38" of the fuel filter 34. The differential pressure sensor 36 records the pressure differential between the inlet 38' and outlet 38" via signals provided on lines 40' and 40" and creates a signal on a differential pressure signal line 56 to communicate the differential pressure to the control system 52 for use in the fuel quality logic. However, in many of the exemplary embodiments disclosed herein, the differential pressure sensor 36 is an optional component and is not necessary to determine whether the fuel filter 34 is functioning properly. In addition, in some embodiments, when the fuel 21 being supplied is determined to be substantially free of water and particulate, the fuel filter 34 may itself become a redundant feature, because there is no contamination in the fuel 21 that requires filtration.

After the fuel 21 leaves the outlet 38" of the fuel filter 34, the fuel 21 enters a particle counter 44, or other particle detector. The particle counter 44 detects particle contaminants, both particulate and free water, in the fuel 21 by physically counting particles and measuring particle dimensions in a sample flow of the fuel stream. The higher the particle count and the larger the particle volume, the lower the fuel 21 quality. If the particle count in the fuel 21 reaches a certain threshold, such as 310 particles of particulate per milliliter in the aviation industry for example, the fuel 21 is deemed to contain too many particles to be safe for use. One example of a particle counter 44 that may be employed in this embodiment is the Hydac Contamination Monitor CS 1000 sensor described at www.hydacusa.com, incorporated herein by reference in its entirety. The particle counter 44 is electrically coupled to the control system 52 via a particle monitor line 60 so that the control system 52 receives the continuous real time particle count in the fuel 21 as fuel dispensing is performed. The control system 52 also uses the particle count in its fuel quality logic. As will be discussed below, some embodiments only require a single particle counter 44 to determine whether the fuel 21 contains unacceptable levels of particulate and/or free water. This may significantly reduce the cost and complexity of the fuel dispenser 14 over existing arrangements.

After the fuel 21 leaves the particle counter 44, the fuel 21 may pass through the optional separate moisture and free water sensor 42. The moisture and free water sensor 42 is placed inline to the fuel conduit 18. The moisture and free water sensor 42 is coupled to the control system 52 via a water sensor line 58. The moisture and free water sensor 42 determines the dissolved water content in the fuel 21 as a function of Relative Humidity (RH) and also measures free water as function of percentage parts-per-million (PPM). By placement of the free water sensor 42 on the outlet side of the particle counter 44, the control system 52 can determine if all moisture or free water was properly absorbed by the fuel filter 34. Thus, the control system 52 can in effect determine the water absorption performance of the fuel filter 34 and generate an alarm or check filter status if the fuel filter 34 is not properly absorbing water. If the free water content of fuel 21 reaches a certain threshold, for example 15 PPM in the United States commercial aviation industry, the fuel is deemed to contain too much free water to be safe for use.

The fuel 21 then continues in the fuel conduit 18 through a manifold 46 that allows a meter 16 to be coupled inline to the fuel conduit 18 on its inlet side. The meter 16 is also coupled to the fuel conduit 18 using another manifold 46 in its outlet side. As the fuel 21 passes through the meter 16, the meter 16 converts the flow of fuel 21 into either an electrical or mechanical signal 48, representing the volume of fuel 21 passing through the meter 16, and communicates this signal to a computer 20 to display the volume of fuel 21 dispensed. The computer 20 may also display the price of the fuel 21 dispensed based on the volume and a set price per unit volume to be charged to the customer.

Note that the fuel filter 34 and particle counter 44 are placed on the inlet side of the meter 16 in this embodiment. This is so that any water or debris that the fuel filter 34 can remove from the fuel 21 is performed before the fuel 21 reaches the meter 16 to be metered. It is generally good practice to avoid metering contaminated fuel, which may be in violation of agreements with customers to be charged for a certain quality of fuel. In addition, contaminants passed through the meter 16 will cause meter wear, thereby making the meter inaccurate over time. This is because the meter 16 is typically a positive displacement meter where a known volume is displaced. Contaminants cause the internal volume to increase, thereby dispensing more fuel than charged when this occurs. As a result, calibration would also be required more often if the fuel filter 34 is not placed on the inlet side of the meter 16.

In this embodiment, the fuel 21 next encounters a fuel flow control valve 50 downstream of the fuel filter 34 and sensing devices 36, 42, 44 of the fuel dispenser 14. It should be understood, however, that the control valve 50 may be upstream of one or more of the fuel filter 34 and sensing devices 36, 42, 44 in other embodiments. The fuel flow control valve 50 may be a conventional on/off valve that is controlled by the control system 52 to open and close, and if opened, to the degree desired. The fuel flow control valve 50 may also be a solenoid controlled proportional valve, if desired, or another type of valve, including those controlled by stepper motors or pneumatically controlled by a delivery vehicle safety system. If the control system 52 allows fuel flow at full flow rate, the control system 52 will send a signal, which is typically a pulse width modulated (PWM) signal in the case of a solenoid controlled proportional valve, over a flow control valve signal line 65 to fully open the control valve 50. If flow is not allowed, the control valve 50 will be closed. If flow is allowed at less than full flow rate, the control valve 50 will be partially closed. As will be discussed later below in the fuel quality logic, the control system 52 controls the fuel flow control valve 50 to execute the fuel control logic to control fuel dispensed. The control of the fuel flow control valve 50 completes the closed loop nature of this embodiment, wherein sensing devices 36, 42, 44 are inputs to the control system to provide an indication of fuel quality and fuel filter 34 status, and the output is from the control system 52 to the fuel flow control valve 50 to control fuel in response. The control system 52 can also generate reports and alarms, drive status indicators, and send messages both locally and off-site to report the status of the sensing devices 36, 42, 44 fuel quality as a result of analysis of the sensing devices 36, 42, 44, according to executed fuel quality logic.

In this regard, the control system 52 may contain an internal clock 64 to use for determining time, or the resolution of accepting or receiving readings from the sensing devices 36, 42, 44, or to perform other time-based functions. The control system 52 also contains user interface electronics 66 that are used to allow the control system 52 to interface to external input and output devices that are customer accessible and either used to access the control system 52 or to provide recording and storage of information. For example, a terminal or computer 68 may be interfaced to the control system 52. This will allow a user to access information about the fuel quality from the control system 52 and program parameters for the fuel quality logic. A database 70 may be provided and interfaced to the control system 52 via the user interface electronics 66 to store fuel quality information and/or information about the sensing devices 36, 42, 44. A printer 72 may be coupled to the control system 52 to print out reports and/or alarms about fuel quality and/or sensing devices 36, 42, 44 readings. Further, the control system 52 may be adapted to send any of this information to a remote system 76 located remotely from the fuel dispenser 14 via data transfer interface 74. These communications may be Internet or telephone based, based either on public or private networks. Further, the control system 52 may contain an antenna 78 that allows wireless communication of the aforementioned information to a wireless transceiver 82 via a modulated RF signal 80, wherein the wireless transceiver 82 contains its own antenna 84 to receive the signal 80.

Now that the components and architecture of one exemplary embodiment of the fuel dispenser 14 have been set forth and discussed, the fuel quality logic that is performed by the control system 52 using measurements and input from the particle counter 44, alone or in combination with other sensing devices 36, 42, to quantify particulate and free water contamination in fuels including but not limited to transportation, aviation, and industrial fuels will now be discussed.

These apparatuses and methods in one embodiment are for use with infrared or laser based particle counters, such as the Hydac CS 1000, in applications to detect particulate and free water in transportation, aviation and industrial fuels. However, these apparatuses and methods can be used in any application where particle counters are used to determine the quality of a suitable liquid.

Automatic particle counters can be used to measure the quality or cleanliness of fuels prior to their consumption in an engine. For aviation fuels, it is particularly important to measure fuel quality when it is actually being loaded onto an aircraft, downstream of all filters and separators. Using particle counters "under the wing" provides final real time analysis of the fuel quality loaded on the aircraft prior to flight and provides an apparatus and method of preventing or limiting poor quality fuel from being loaded.

Current generation commercially available particle counters measure the number of particles (water and particulate) per milliliter of fuel and report the data in three different size range categories: ≥4 μm, ≥6 μm, and ≥14 μm. However, due to current industry practices, it may be desirable to report the water concentration in parts per million (PPM) and particulate concentration in mg/L rather than particle counts. In addition, next generation particle counters are capable of reporting in four different size categories: ≥4 μm, ≥6 μm, ≥14 μm, and ≥21 μm. As will be discussed in detail below, the embodiments described herein may be adapted to be used with a variety of different types of particle counters and reporting mechanisms, to determine particulate and/or water concentration in a number of different ways based on these and other mechanisms.

Currently available particle counters, such as particle counter 44, do not directly distinguish between water and particulate contamination in fuels. This disclosure and embodiments described below describe apparatuses and methods to analyze particle counter data using predetermined empirical data to uniquely distinguish the presence of water or particulate and to quantify the amount of each in the fuel using information from a single particle counter 44.

Particle counters are common contaminant-measuring instruments found in the condition monitoring industry. Particle counter 44 in FIG. 2 is one example of a particle counter. Particle counters have a long history of successful use in hydraulic and lubrication (laboratory) applications, but are relatively new to aviation and other transportation fuels.

Figure 3:
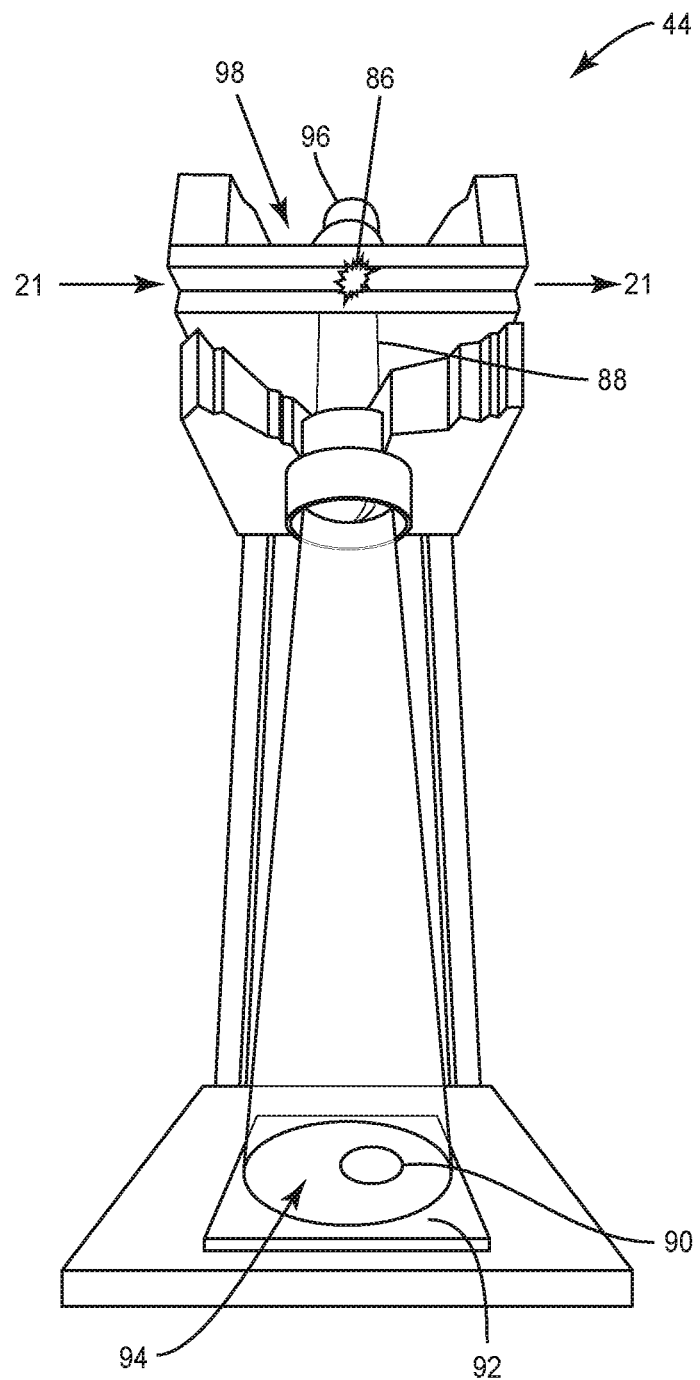
FIG. 3 is a schematic diagram of an exemplary particle sensor.
Figure 4:
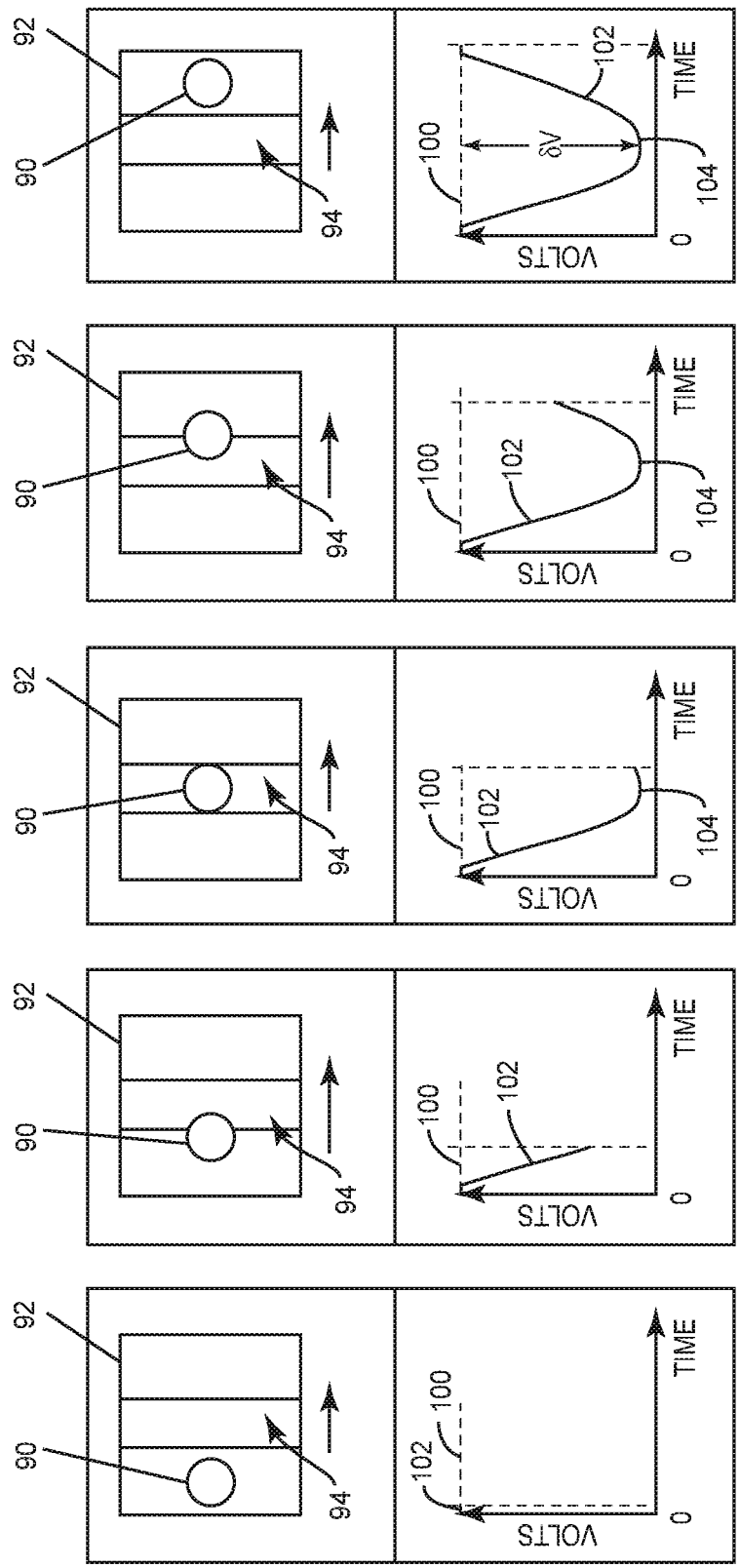
FIGS. 4A-4E are a sequence of diagrams illustrating a particle traversing a sensing zone of a particle sensor with corresponding plots of sensor voltage as the particle traverses the sensing zone.

Most commercial particle counters (sometimes referred to as Automatic Particle Counters, APCs) use the principle of light obscuration. As shown in FIG. 3, a particle 86 flows through a light beam 88 and casts a shadow 90 on a photoelectric sensor 92. Each shadow 90 constitutes a single count, and the reduction in light intensity on the sensing zone 94 of the sensor 92 is correlated with the size of the particle. The photoelectric sensor 92 measures every discrete particle 86 passing through the light beam 88 and sorts the results to yield the number of particles 86 of a given size range per unit volume of fuel sample.

A typical particle counter 44 layout has a light source 96 that directs the light beam 88 through an optical cell 98. A sample of the fuel 21 flows through the optical cell 98 (which may be only 200 microns in cross-section), such that the light beam 88 passes through the fuel 21 toward a photoelectric sensor 92. The flow rate through the particle counter 44 is specific to the particular instrument and is fixed within manufacturer limits.

It is desirable that only one particle 86 appears in the sensing zone 94 at any single point in time. If two or more particles 86 pass through the light beam 88 simultaneously, the result will be affected. This condition is known as the "point of coincidence" and is the practical limit of this method of measuring particle count in fuel. However, if fuel 21 contains enough contamination to reach the point of coincidence for currently available particle counters 44, this would represent a heavily contaminated sample well beyond the limits of industry standards for fuel cleanliness. In practice, such heavily contaminated fuel is likely to be detected by other means prior to fueling, e.g., by fuel quality sensors in the fuel tank 12. Thus, the point of coincidence of currently available particle counters 44 may be effectively ignored in these and other embodiments.

FIGS. 4A-4E schematically illustrate the sequence of a (spherical) particle 86 (not shown) traversing the sensing zone 94, with corresponding plots of the drop in sensor voltage as the particle 86 casts a shadow 90 on the sensing zone 94. The bigger the particle 86, the bigger the shadow (area) 90 and the bigger the voltage reduction (i.e., the voltage "spike") as the particle 86 traverses the sensing zone 94.

In FIG. 4A, the particle 86 is not between the light beam 88 (not shown) and sensing zone 94 of sensor 92. Thus, any shadow 90 cast by the particle 86 is outside the sensing zone 94, and the voltage from the sensor 92 remains at a baseline level 100 as a result. As the particle 86 passes between the light beam 88 and the sensing zone 94, however, voltage 102 drops accordingly. As shown by the sequence of FIGS. 4B-4E, the voltage 102 drops as the shadow 90 enters the sensing zone 94 (FIG. 4B) to voltage minimum 104 when the entire shadow 90 is within the sensing zone 94 (FIG. 4C). As the shadow 90 exits the sensing zone 94 (FIG. 4D), the voltage 102 increases until the shadow 90 has exited the sensing zone 94 (FIG. 4E) and the voltage 102 has returned to the baseline level 100. The measured reduction in light intensity on the sensor when the voltage 102 reaches the voltage minimum 104 is expressed as δV for each shadow 90.

Each shadow 90 constitutes a single particle count and the measured reduction in light intensity on the sensor, δV, is correlated with a projected area, $A_p$ (k is a sensor constant).

$$\delta V = k A_p$$

The projected area is equated to the area produced by a sphere ("equivalent sphere"—see below for more detail) of diameter $d_p$—this is the "particle size."

$$A_p = \frac{\pi d_p^2}{4}$$

$$\therefore \delta V = k \frac{\pi d_p^2}{4}$$

Accordingly, the value of the voltage spike, δV, varies directly and exponentially with particle diameter, $d_p$. However, rather than develop complex algorithms to calculate $d_p$, the particle sizing industry has adopted a correlation method using specified calibrants (known in the industry as ISO 11171).

Each voltage "spike" corresponding to a single particle is counted and these counts are grouped or "channelized" according to their calculated sizes. This grouping provides a particle size distribution—the result is a number of particles within a given size range per milliliter of fuel.

Microscopists were the first to systematically measure very small particle sizes, and they did so by assessing the longest length of a particle, i.e., its longest chord (in microns, μm). When instrumental methods became more common, users continued with the same measurement system as the microscopists, formalized by ISO 4402.

The later introduction of the Scanning Electron Microscope gave microscopists a new tool capable of measuring the projected area of a particle. To simplify particle size analysis, a methodology was developed to take the measured area of the particle and calculate the diameter of a sphere of equivalent area. This methodology is formalized by ISO 4406 and ISO 11171. To differentiate this new methodology from the longest chord method, micron (c) is used. This has many benefits over the longest chord method when dealing with particles of various shapes. For instance, there would no longer be a risk of "needle-shaped" contaminants being misinterpreted as large spheres.

Regardless of the method of area calculation, these particle counters measure the profile dimensions of each scanned particle and calculate an equivalent diameter of a sphere that would project an area equivalent to the area of the measured particle, regardless of its actual shape.

The measured particle sizes and size distributions received from the particle counter 44 may be combined with empirical data corresponding to similar measured particle sizes and size distributions to determine a number of fuel quality conditions. For example, as will be discussed in detail below, total mass and volume of particles in each size channel may be determined based on the returned ISO codes and previously recorded empirical measurements for each size channel. The ratios between the measured mass and/or volume of particles in different channels may also be used with empirical data to determine whether the measured particles contain free water, and if so, relative distributions of water and particulate in fuel. In this manner, measurements from a single particle counter 44 can be used to determine whether particulate is above a first threshold, and can also be used to determine whether water contamination is above a second, different threshold.

Figure 5:
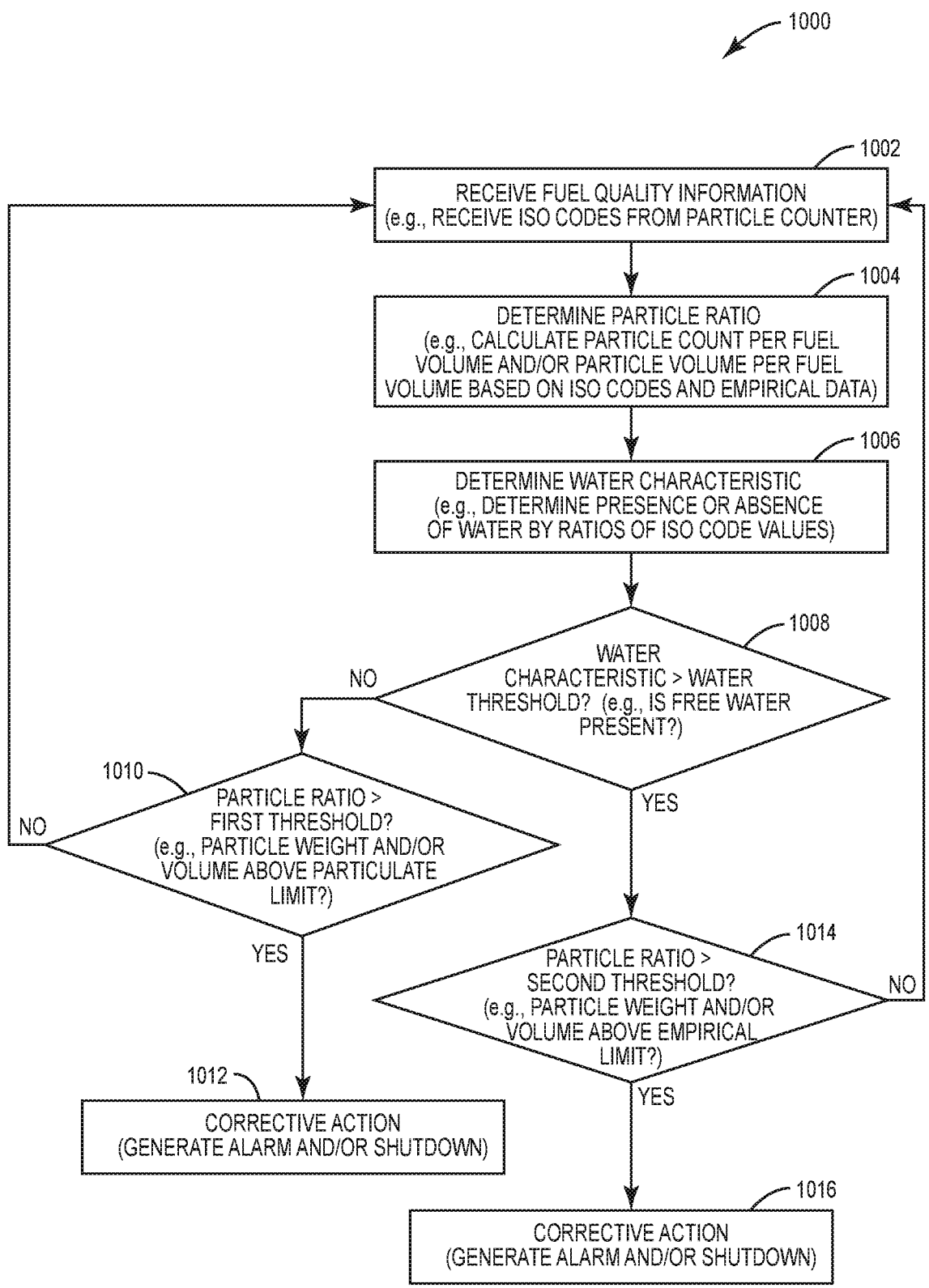
FIG. 5 is a flowchart illustrating an exemplary process for determining, based on fuel quality information received from a particle sensor in real time, whether to initiate corrective action based on measured fuel quality conditions.

In this regard, FIG. 5 illustrates a simplified flowchart of an exemplary process 1000 for determining contamination levels in fuel according to an embodiment. Before discussing each step in detail, an overview of process 1000 is described. In this regard, during process 1000, fuel quality information is received (Block 1002). Next, a particle ratio is determined (Block 1004), and a water characteristic is determined (Block 1006). The water characteristic is then compared to a water threshold (Block 1008). If the water characteristic does not exceed the water threshold, the particle ratio is compared to a first particle threshold (Block 1010). If the particle ratio exceeds the first particle threshold, corrective action is taken (Block 1012). If the particle ratio does not exceed the first particle threshold, the process returns to the step of receiving fuel quality information (Block 1002). Referring back to the comparison of the water characteristic to the water threshold (Block 1008), if the water characteristic does exceed the water threshold, the particle ratio is compared to a second particle threshold (Block 1014). If the particle ratio exceeds the second particle threshold, corrective action is taken (Block 1016). If the particle ratio does not exceed the second particle threshold, the process returns to the step of receiving fuel quality information (Block 1002).

Turning now to the step of receiving fuel quality information (Block 1002), such information may include, without limitation, receiving a plurality of ISO codes from a particle counter. In one embodiment, the at least one fuel quality characteristic may be at least one number of particles, at least one volume of particles, and/or at least one mass of particle in at least one predetermined particle size range detected by the particle detector.

The step of determining the particle ratio (Block 1004) may include, without limitation, calculating a particle count per fuel volume, calculating a particle volume per fuel volume, and/or calculating a particle mass per fuel volume based on the ISO codes and on empirical data correlating the ISO codes to specific particle counts and/or particle volumes. In one embodiment, determining the particle ratio may comprise determining a total mass of particles in each of the two or more predetermined particle size ranges, based on at least one number of particles in each of the at least two predetermined particle size ranges and on a respective predetermined empirical mass and/or volume constant representing an approximation of an average mass and/or volume of particles in the respective predetermined particle size range.

The step of determining a water characteristic (Block 1006) may include, without limitation, determining the substantial presence or absence of free water in the fuel based on one or more ratios between the different ISO code values and/or particle properties calculated from the ISO code values. In one embodiment, a separate water sensor, such as a moisture sensor, may be used to detect the substantial presence or absence of free water. In another embodiment, the same particle counter used to determine the particle ratio in Block 1014 may be used to also determine the water characteristic. In one example, the water characteristic may an approximate ratio of a total mass and/or volume of particles in a first particle size range of the at least two predetermined particle size ranges by the particle detector to a total mass and/or volume of particles in a second particle size range of the at least two predetermined particle size ranges. As will be discussed in detail with respect to FIG. 7 below, both the particle ratio and water characteristic may be determined using a single particle detector, thereby reducing the cost and complexity of the system. As discussed above, the step of comparing the water characteristic to the water threshold (Block 1008) may include, without limitation, determining whether free water is present in the fuel.

The step of comparing the particle ratio to the first particle threshold (Block 1010) may include, without limitation, determining whether the particle count, particle weight, and/or particle volume per unit volume of fuel is above a predetermined particulate limit. The step of taking corrective action (Block 1012) may include, without limitation, generating an alarm condition and/or initiating shutdown of the fueling process. Initiating shutdown may include automatically reducing or preventing flow of fuel through the fuel conduit.

The step of comparing the particle ratio to the second particle threshold (Block 1014) may include, without limitation, determining whether the particle count and/or particle volume per unit volume of fuel is above a predetermined empirical limit. The step of taking corrective action (Block 1016) may include, without limitation, generating an alarm condition and/or initiating shutdown of the fueling process. It should be understood that the corrective action of Block 1016 may be the same type of corrective action taken in Block 1012, or may be a different type, as desired.

In this manner, a control system employing the method of FIG. 5 may be configured to periodically repeat the steps of determining the particle ratio and the first water characteristic in response to a determination not to initiate the at least one corrective action.

Figure 6:
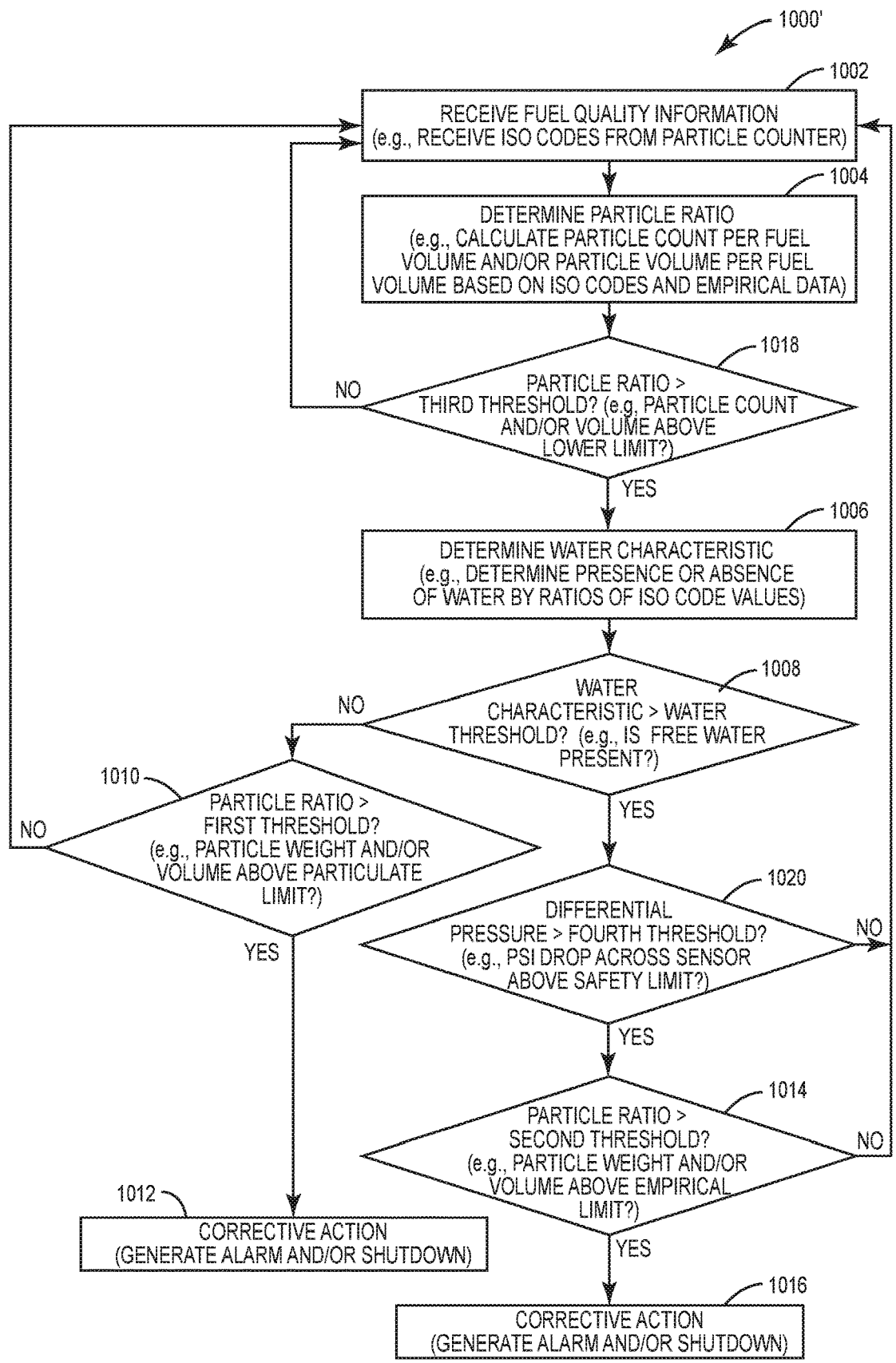
FIG. 6 is a flowchart illustrating an alternative exemplary process similar to the process of FIG. 5, in which a determination in real time that fuel quality is safe may halt further processes for determining whether to initiate corrective action.

The process may also include additional steps, as desired. In this regard, FIG. 6 illustrates a flowchart of an exemplary alternative process 1000' according to another embodiment. During alternative process 1000', fuel quality information is received (Block 1002). Next, a particle ratio is determined (Block 1004). In this embodiment, however, before the water characteristic is determined (Block 1006), the particle ratio is compared to a third particle threshold (Block 1018). If the particle ratio exceeds the third particle threshold, the water characteristic is determined (Block 1006). If the particle ratio does not exceed the third particle threshold, the process returns to the step of receiving fuel quality information (Block 1002). The water characteristic is then compared to a water threshold (Block 1008). If the water characteristic does not exceed the water threshold, the particle ratio is compared to a first particle threshold (Block 1010). If the particle ratio exceeds the first particle threshold, corrective action is taken (Block 1012). If the particle ratio does not exceed the first particle threshold, the process returns to the step of receiving fuel quality information (Block 1002). Referring back to the comparison of the water characteristic to the water threshold (Block 1008), if the water characteristic does exceed the water threshold, differential pressure information is compared to a differential pressure threshold (Block 1020). If the differential pressure information does not exceed the differential pressure threshold, fueling continues and the process returns to Block 1002. If the differential pressure information exceeds the differential pressure threshold, the process continues and a particle ratio is compared to a second particle threshold (Block 1014). If the particle ratio exceeds the second particle threshold, corrective action is taken (Block 1016). If the particle ratio does not exceed the second particle threshold, the process returns to the step of receiving fuel quality information (Block 1002).

The step of comparing the particle ratio to the third particle threshold (Block 1018) may include, without limitation, determining whether a particle count and/or particle volume per fuel volume is above a lower, "safe" particle limit. If the particle count and/or particle volume is not above the "safe" particle limit, the process can cycle back to Block 1002.

The step of comparing the differential pressure information to the differential pressure threshold (Block 1020) may include, without limitation, determining whether a measured pressure drop across a fuel filter exceeds a safe level. In one embodiment, as discussed above, a fuel filter having a fuel input and a fuel output is disposed along the fluid flow path, and a differential pressure sensor is configured to measure a pressure differential between the fuel input and the fuel output of the fuel filter. The electronic control system may be configured to receive differential pressure information corresponding to the pressure differential from the differential pressure sensor in real time, and repeat the steps of determining the particle ratio and the first water characteristic prior to determining whether to initiate the at least one corrective action, based on the differential pressure information.

As discussed above, different fuel quality characteristics may be determined in real time as fuel is delivered. In this regard, exemplary methods for determining a number of different fuel quality characteristics for use with the above processes are described below. As discussed above with respect to FIGS. 3 and 4, currently available particle counters 44 provide information in the form of ISO codes, such as, for example, ISO 4406. ISO 4406 is the three-part code for reporting particles measured by APCs, automatic particle counters, calibrated in accordance with NIST Standard Reference Material (SRM) 2806. The 'ISO cleanliness code' is comprised of three scale numbers which permit the differentiation of the size and the distribution of the particles. The first number represents the total number of particles equal to and greater than 4 µm (c) per milliliter of fluid. The second number represents the total number of particles equal to and greater than 6 µm (c) per milliliter of fluid. The third number represents the total number of particles equal to and greater than 14 µm (c) per milliliter of fluid. An APC reports these size channels for the same mL of fluid. The allocation scale numbers are shown in the chart 120 in Chart 1 below.

CHART 1

| Number of particles per milliliter | | |
|---|---|---|
| More than | Up to and including | Scale number |
| 2 500 000 | — | >28 |
| 1 300 000 | 2 500 000 | 28 |
| 640 000 | 1 300 000 | 27 |
| 320 000 | 640 000 | 26 |
| 160 000 | 320 000 | 25 |
| 80 000 | 160 000 | 24 |
| 40 000 | 80 000 | 23 |
| 20 000 | 40 000 | 22 |
| 10 000 | 20 000 | 21 |
| 5 000 | 10 000 | 20 |
| 2 500 | 5 000 | 19 |
| 1 300 | 2 500 | 18 |
| 640 | 1 300 | 17 |
| 320 | 640 | 16 |
| 160 | 320 | 15 |
| 80 | 160 | 14 |
| 40 | 80 | 13 |
| 20 | 40 | 12 |
| 10 | 20 | 11 |
| 5 | 10 | 10 |
| 2.5 | 5 | 9 |
| 1.3 | 2.5 | 8 |

By definition, the ≥4 µm channel is the largest as it includes all particles counted by the particle counter. The ≥6 µm channel is the next largest number and excludes all particles <6 µm. The ≥14 µm channel is the smallest.

However, ISO 4406, through filtering, loses some information available in the raw particle counts required for the method. Fortunately, most APC manufacturers use decimal tenths in reporting ISO 4406 to preserve a path to reconstruct the raw counts as described in the exemplary method below.

Step 1

Convert the APC 3 size channels from ISO code values per milliliter to raw particle counts per milliliter. This is accomplished by extrapolating each channel value (including the tenth decimal value) logarithmically based on the ISO 4406 size allocation chart above.

Step 2

Redefine the size channels as follows:
Channel 1: ≥4 µm to <6 µm (subtract ≥6 µm counts from ≥4 µm counts)
Channel 2: ≥6 µm to <14 µm (subtract ≥14 µm counts from ≥6 µm counts)
Channel 3: ≥14 µm

Step 3

Identify particle size distribution using the APC to empirically calculate mean particle diameter within each size channel.
Results for test system:
Channel 1: 4.8 µm
Channel 2: 9.5 µm
Channel 3: 19.98 µm (revised from 17.5 µm based on empirical testing)
It should be understood that Channel 1 and 2 diameters could be just as easily defined as the middle of the channel range; i.e. Channel 1=5 µm (middle of 4-6 µm range) and Channel 2=10 µm (middle of 6-14 µm range) with modest changes to the volume results. The Channel values 2 and 3 are the most important calculated empirically and may vary depending on the fuel pump speed and type of particulate.

These three (3) diameters are used to calculate the total volume of particles for each channel per mL.

$$\text{Total Volume/mL} = (\text{Channel particle count}) * \frac{4}{3}\pi(d/2)^3$$

Since the particles are calculated and reported by the APC as counts per milliliter in this embodiment, a conversion to parts per million can be performed. Laboratory tests were performed exclusively with water and exclusively with particulate providing a large database to confirm assumptions. Accurately measured and dispensed quantities of each contaminate were introduced to controlled flow rates of fuel. These tests were used to empirically validate the calculated contaminations.

Figure 7:
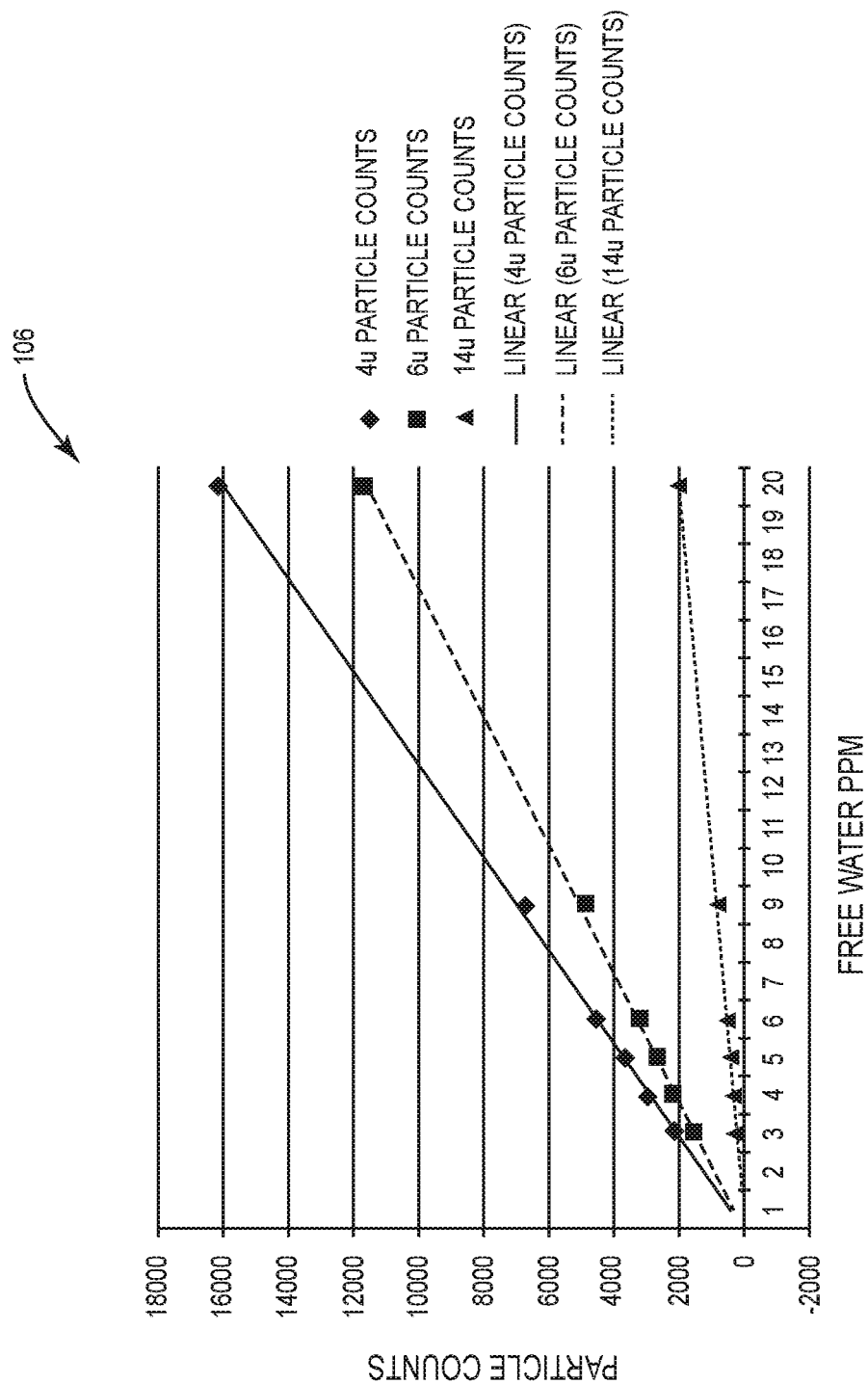
FIG. 7 is a chart depicting an exemplary empirically derived plot of particle counts per milliliter vs. free water PPM.

In this regard, FIG. 7 is a chart 106 depicting exemplary test results with free water at various contamination rates (PPM). Note that the three (3) particle counter channels are not filtered, meaning that the 4 μm channel represents the number of all particles larger than 4 μm and is not the number of particles larger than 4 μm, but less than 6 μm. The same is true for the 6 μm channel in this embodiment.

It was apparent from this data that the relationship of particle counts by channel to increasing free water PPM is linear, as shown by the linear trendlines corresponding to each channel in FIG. 7. In this example, the 4 μm channel increases 851 particles counts per 1 PPM of free water increase; 6 μm channel increases 665 counts per PPM; and the 14 μm channel increases 106 counts per PPM.

Figure 8:
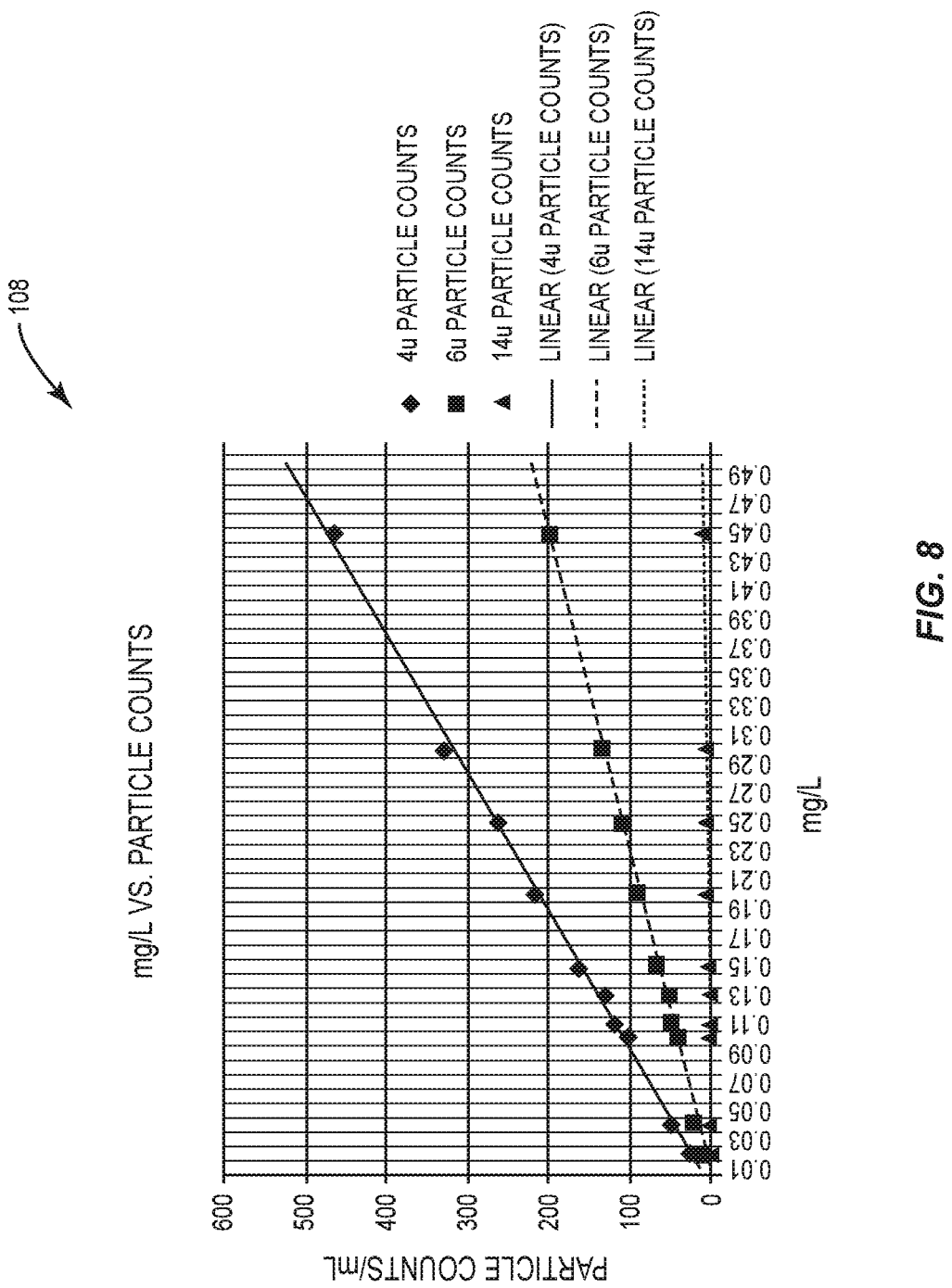
FIG. 8 is a chart of an exemplary empirically derived plot of particle counts per milliliter vs. milligrams per Liter (mg/L) of particulate in fuel.

FIG. 8 is a chart 108 depicting exemplary test results with particulate at various contamination rates (mg/L). As with free water, in this example, note that the three (3) particle counter channels are not filtered, meaning that the 4 μm channel represents the number of all particles larger than 4 μm and is not the number of particles larger than 4 μm, but less than 6 μm. The same is true for the 6 μm channel.

Also, as with free water, the relationship of particle counts by channel to increasing particulate mg/L is linear. The 4 μm channel increases 104 particles counts per 0.1 mg/L of particulate increase; 6 μm channel increases 44.6 counts per 0.1 mg/L; and the 14 μm channel increases 2.6 counts per 0.1 mg/L.

Since the relationship of both free water and particulate are linear with respect to particle counts but have significantly different slopes, it is possible to distinguish which is present in the fuel. Although there are different methods that may be employed, in this embodiment the volume ratio of 14 μm/(4 μm-6 μm) is used to determine the presence of free water or particulate. From empirical data, the following relationship is used:

14 μm/(4 μm-6 μm)>40=Dominant Presence of Free water

14 μm/(4 μm-6 μm)<6=Dominant Presence of Particulate

14 μm/(4 μm-6 μm)<40, >6=Combination of both Free Water and Particulate

Empirical testing has also found that in many use cases, the following relationship may be used:

14 μm/(4 μm-6 μm)>10=Dominant Presence of Free water

14 μm/(4 μm-6 μm)<5=Dominant Presence of Particulate

14 μm/(4 μm-6 μm)<10, >5=Combination of both Free Water and Particulate

Using this relationship has a number of advantages. First, narrowing the "combination" range, in which it is not clear whether free water or particulate is dominant, allows for more efficient testing and delivery of aircraft fuel, without significantly affecting the accuracy of the test. Second, when the 5-10 ratio range is encountered in practice, it is usually for a very short duration, with the ratio quickly changing to a value below 5 (indicating particulate) or above 10 (indicating free water).

An additional filter may also be employed to indicate the presence of water or particulate requiring that the first threshold be exceeded.

It is observed in this example that any amount of free water above 1 PPM will "hide" any amount of particulate present in the fuel (at least within industry limits of particulate range, 0.3 mg/L). For example: a first aviation industry threshold for concern or alarm with particulate is 0.15 mg/L of fuel. At this level, with no free water present in the fuel, the particle counter would have a 4 μm channel reading of about 155 counts. The industry threshold for free water concern is 15 PPM. At this level, with no particulate present in the fuel, the particle counter would have a 4 μm channel reading of about 12,770 counts. Or looked at another way, 1 PPM of water has a 4 μm channel count of 850; more than 5 times the counts for 0.15 mg/L for the first particulate threshold. Whenever the volume ratio of 14 μm/(4 μm-6 μm) channels is above 35, there is no possible way for the particle counter to measure or account for particulate.

However, if the particle counter showed no or low (acceptable) levels of particulate prior to a free water event, it is very important to monitor the differential pressure across the fuel filter for any rise or drop in differential pressure. If no pressure rise above differential pressure threshold of 15 psi or drop of 5 psi below recent steady state differential pressure for given flow rate occurs, it is reasonable to assume that there is no increase in particulate and the issue of free water can be addressed independently. The particulate is not directly observed when free water is above 1 PPM, but this embodiment can measure the differential pressure to ensure there is no particulate contamination concurrent with the increase in free water. Also, the linear relationship between the channels may not be different or unique to each manufacturer of particle counters as they use different methods to process data.

Also, note that the ratio thresholds shown above may be modified for different pumping systems. It is reasonable to believe that pumps with slower or faster rpm than the one used in the present test data could create different size distribution free water particles. It is believed that these changes will not be significant, as data collected from the other tests indicate similar ratios.

In this example, relative humidity (moisture sensor) is not used in any of our calculations. Using relative humidity can be slow when compared to the particle counter. Regardless, there is a way to definitively identify water on one processor scan. The moisture sensor can be kept in the system because the saturated water in the fuel is a valuable parameter to have, and the particle counter cannot detect saturated water.

As an example, the aviation industry is concerned that adoption of particle counters for dynamic under wing analysis of fuel quality will likely cause many "false positive" events where short duration events, especially with free water, may cause expensive and unnecessary refueling system shutdowns. The embodiments disclosed herein include methods to totalize the quantity of all free water or particulate and continuously report the cumulative result in real time. Said another way, free water will be reported as PPM for the total delivery up to the current point in time rather than the instantaneous PPM that may be present for short durations of time. The same is done for particulate, which is reported in mg/L for the entire delivery up to the current point in time.

FIG. 8 depicts a chart 108 of exemplary test results from the Energy Institute (EI) protocol test for particle counters used in aviation fuel testing, showing cumulative results for both particulate and water.

The test protocol in this example includes the following parameters:

| Time | Contaminate |
| --- | --- |
| 0-3 minute | Clean fuel no contaminate |
| 3-8 minute | 0.3 mg/L particulate |
| 8-13 minute | 0.15 mg/L particulate |
| 13-18 minute | 0.15 mg/L particulate + 15 PPM free water |
| 18-23 minute | 15 PPM free water |
| 23-28 minute | 30 PPM free water |
| 28-33 minute | Clean fuel no contaminate |

Figure 9:
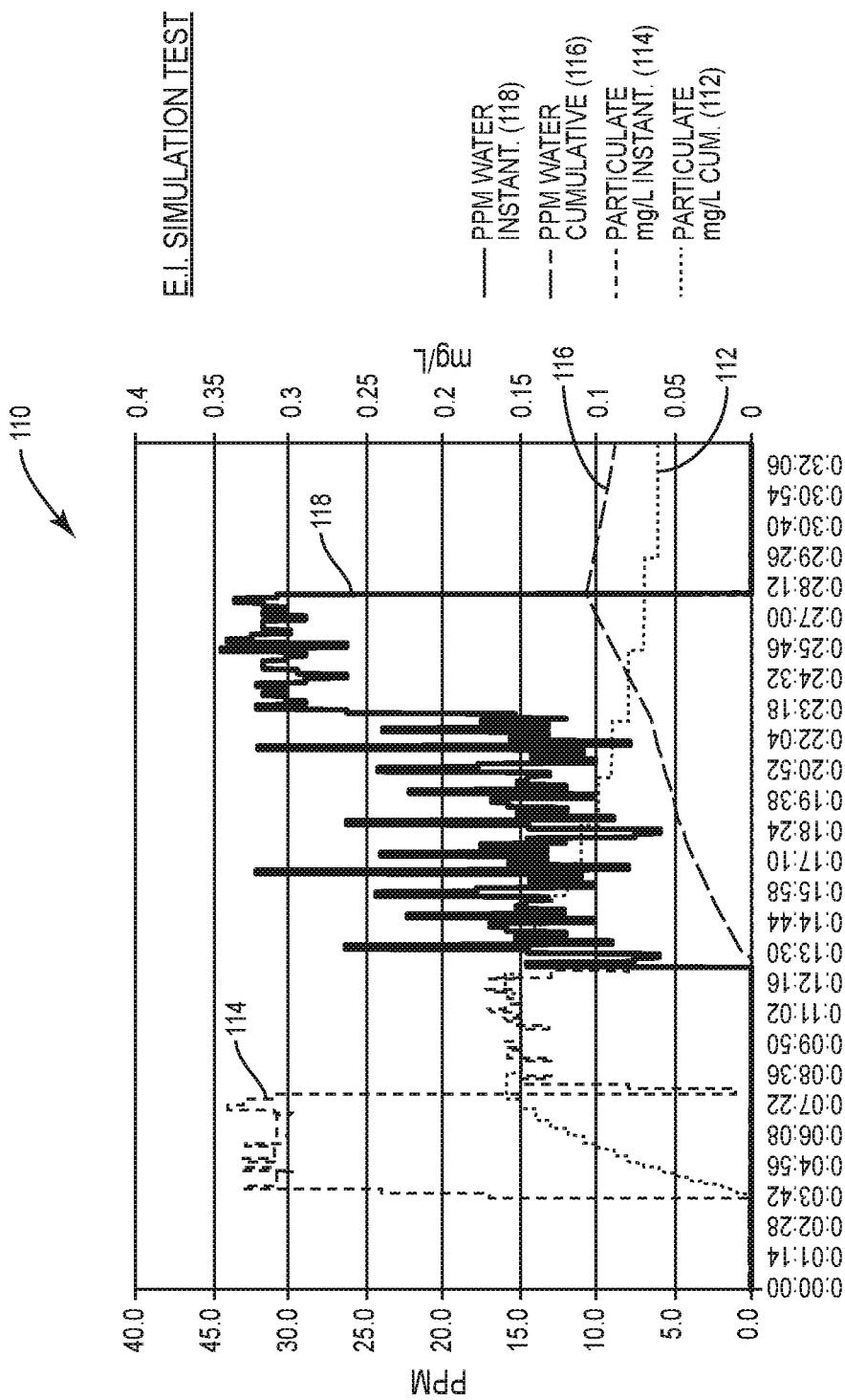
FIG. 9 is a chart of an exemplary test of a fueling event showing instantaneous and cumulative results of particulate and water.

In this example, the system considers the complete thirty-three (33) minute E.I. test a single aviation fueling event; i.e. one aircraft refueling. In this regard, FIG. 9 is a chart 110 of an exemplary test of a fueling event showing instantaneous and cumulative results of particulate and water. It should be noted that the trace 112 in the chart 110 in FIG. 9 represents the cumulative result for all particulate above 4 µm. Although the particle counter quickly identified the particulate at 0.30 mg/L instantaneous (real time reading) at the three minute mark, three minutes of clean fuel had already been loaded on the aircraft, thus diluting the cumulative effect. The cumulative particulate results 112 reach 0.16 mg/L at the six (6) minute mark when the particulate rate is reduced to 0.15 mg/L. Since the instantaneous rate 114 and the rate of cumulative results 112 are equal at this point in time, the cumulative particulate rate is maintained at the level to the thirteen (13) minute mark. At that point, 15 PPM of free water is introduced to the fuel rendering the particle counter "blind" to the particulate. Accordingly, both the instantaneous and cumulative traces 112, 114 are abandoned. The values are not really zero, they are unknown. Note the cumulative trace 116 and the instantaneous trace 118 for the free water. The slope for the cumulative trace 116 increases at the twenty-three (23) minute mark when the free water is increased to 30 PPM. Note also that when water was first introduced at the thirteen (13) minute mark, thirteen (13) minutes of fuel flow at 14 gallon/minute or about 182 gallons of "dry" fuel had already been loaded onto the aircraft, thereby diluting the cumulative effect of the water. Note also the declining cumulative slope once the free water contamination is stopped at the twenty-eight (28) minute mark. This chart indicates that the cumulative amount of water for the entire loading is about 9 PPM.

Cumulative results 112, 116 are calculated and recorded every two (2) seconds. Two methods have been developed to produce cumulative results. The first requires flow data from an external flow meter pulser every 2 seconds. The second method does not, in this example.

In Step 1 of this method (above), it is disclosed how to calculate the volume of contaminate in a single milliliter of fuel by using the particle counts from each APC channel, empirically developing average diameters for the particles in each range and using these diameters to calculate the volume of an equivalent sphere. By adding the total channel volumes together, the approximate total volume of contaminate in one milliliter of fuel is obtained every two (2) seconds, in this example. From this result the PPM of water can be directly derived.

Figure 10:
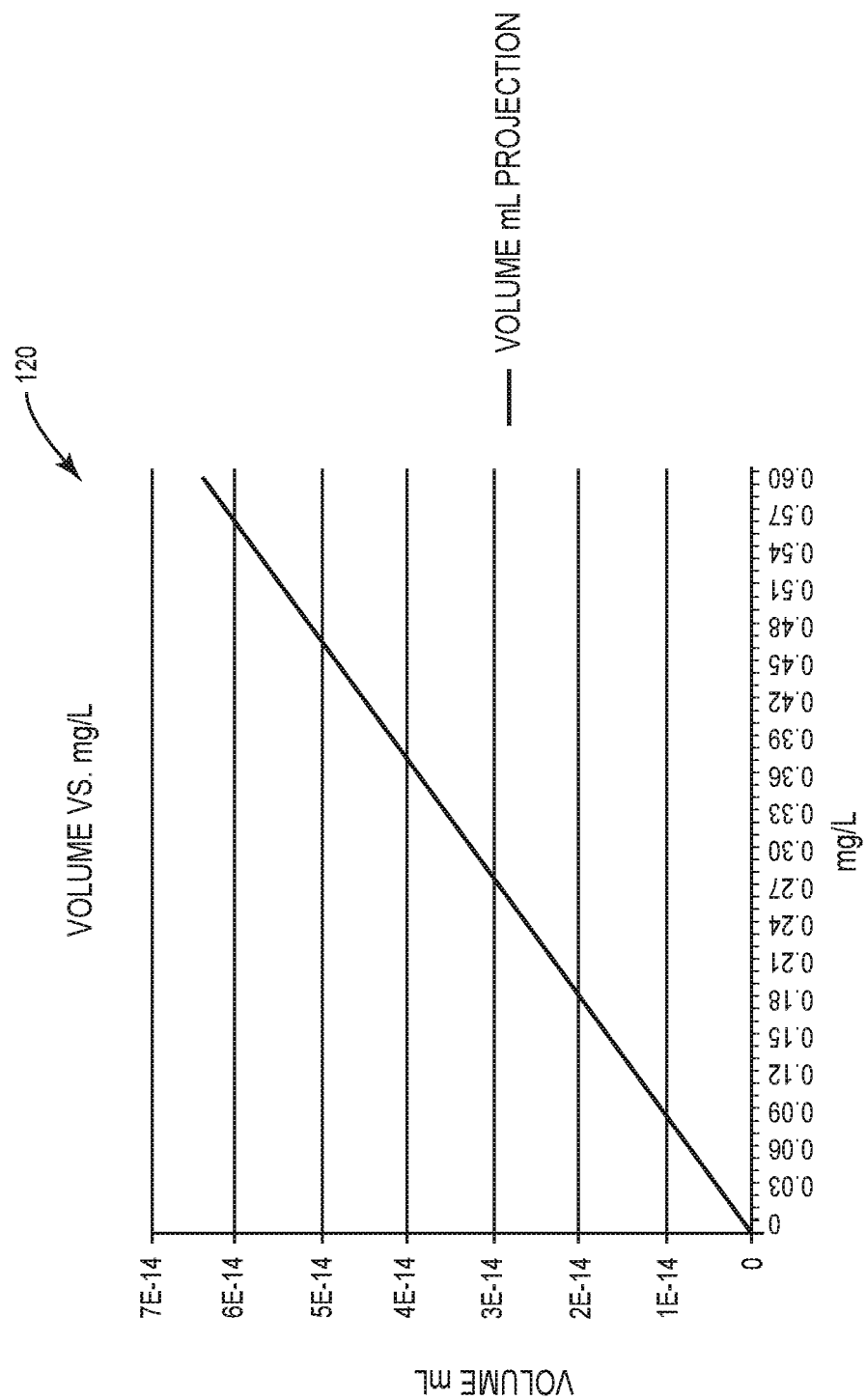
FIG. 10 is a chart of an exemplary empirically derived plot of volume vs. milligrams per Liter (mg/L) of particulate in fuel.

With the addition of flow meter data, one can calculate the flow rate of the fuel for the relevant time period, every two (2) seconds for example, to coincide with the particle counter data. Converting the flow data to milliliters of flow in 2 seconds provides the solution to calculating the total volume of contaminates for that 2 second period of time. Converting contaminate volume to mg/L requires interpolating the results with the chart 120 shown in FIG. 10. This chart 120 in FIG. 10 was developed empirically, and may be unique to each APC manufacturer. It is important to note that this method can automatically adapt to changes in the size distribution of the particles and could be desirable for accommodating different fuel pumping systems or changes in particulate size distribution differing from the ISO A2 dust specification.

Figure 11:
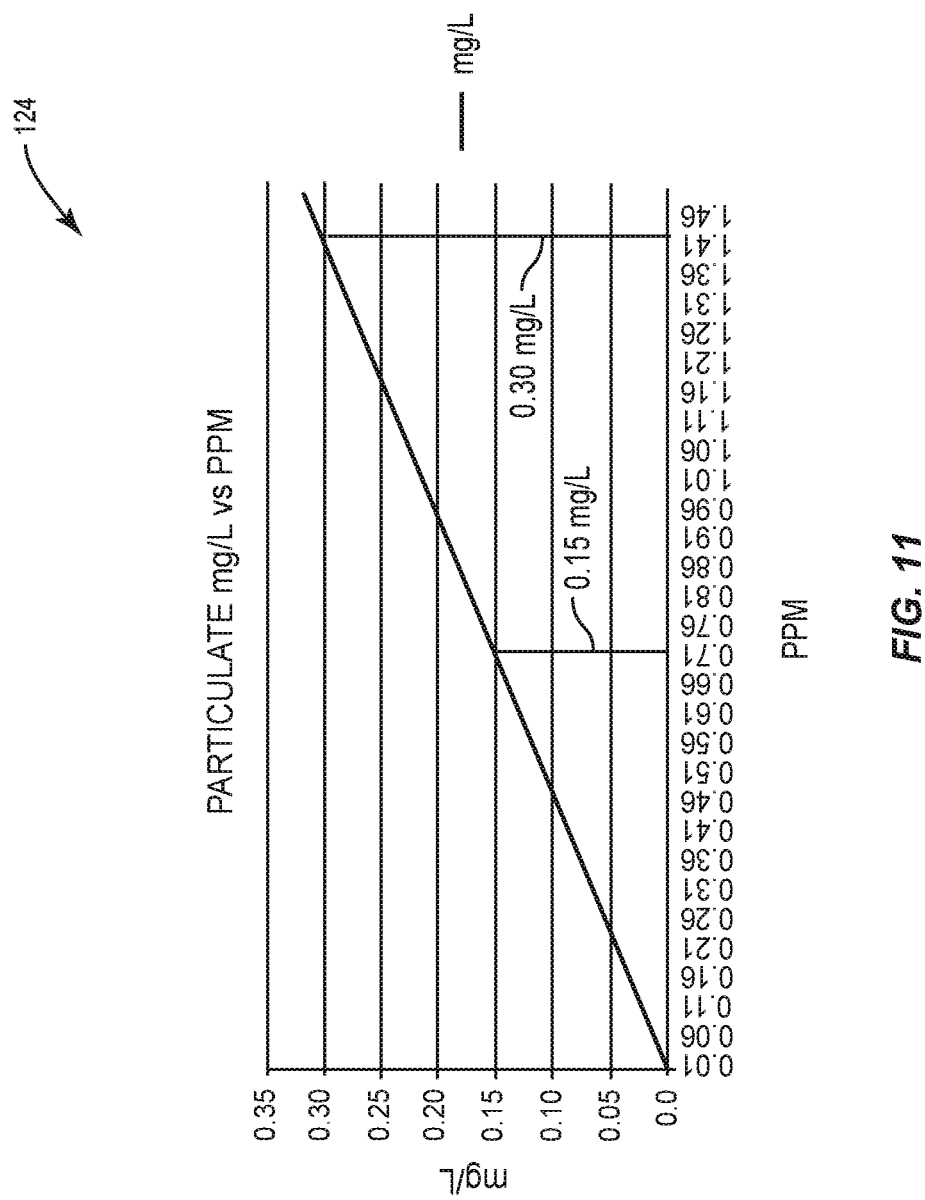
FIG. 11 is a chart of an exemplary empirically developed plot of the relationship between mg/L and PPM for particulates.
Figure 12:
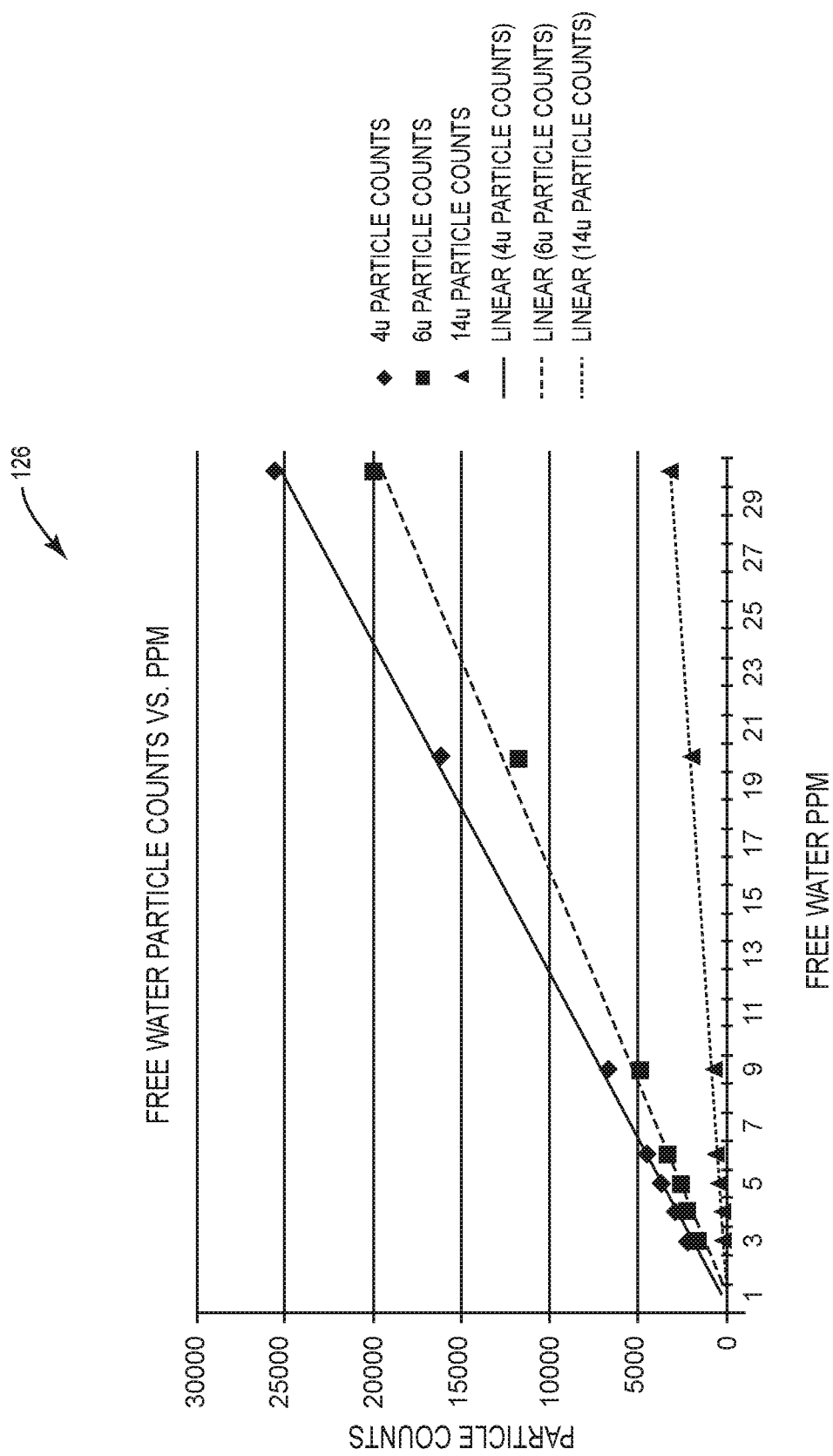
FIG. 12 a chart of an exemplary empirical interpolation of the relationship between particle counts and PPM for free water.

The embodiments disclosed herein also involve a method to calculate the cumulative effects of contaminates without the use of external fuel flow data. Rather than calculating the volumes of contaminates from the APC, charts are used to interpolate particulate mg/L and free water PPM directly from the particle counts. In this regard, referring back to FIG. 8, chart 108 was developed empirically and indicates the relationship between particle counts and mg/L for particulates based on EI standards and ISO A2 Fine Dust. Interpolating the unfiltered 4 µm channel count from the APC, chart 108 in FIG. 8 is used to directly indicate the appropriate mg/L value. Similarly, the chart 124 in FIG. 11 was developed empirically and indicates the relationship between particle counts and PPM, with specific calculations for PPM corresponding to a 0.15 mg/L rate, and to a 0.30 mg/L rate. Likewise, chart 126 in FIG. 12 illustrates a similar empirical interpolation of the relationship between particle counts and PPM for free water. Interpolating the unfiltered 4 µm channel count from the APC is used to directly indicate the appropriate mg/L value.

The embodiments disclosed herein can be implemented in any fuel dispenser. Any type of control system may be used with the embodiments disclosed herein. The control system may be located on the fuel dispenser 14 or may be located in a separate location either proximate the fuel dispenser 14 or remotely. The control system may be accessed by a user either on-site or remotely.

The embodiments disclosed herein may also be employed on a hydrant cart refueling truck that obtains its fuel to delivery from a separate storage tank. The embodiments disclosed herein, and particularly the control system and the components necessary to determine the fuel quality and related statuses described above, may also be provided on a new refueling truck during manufacture, or may be retrofitted to existing refueling trucks. Further, the control system and/or monitoring devices of the embodiments disclosed herein may be powered by a power system on the refueling truck, an external source, or by battery power as examples.

Those skilled in the art will recognize improvements and modifications to the preferred embodiments of the embodiments disclosed herein. All such improvements and modifications are considered within the scope of the concepts disclosed herein.

What is claimed is:

1. A fuel dispensing apparatus for delivering fuel, comprising:
   a flow conduit defining a fluid flow path from a fuel source to an outlet where fuel is dispensed;

a particle detector configured to detect particles in the fuel and generate raw particle counts for each of a plurality of predetermined particle size ranges in real time as the fuel passes through the flow conduit, the plurality of predetermined particle size ranges comprising a first predetermined particle size range and a second predetermined particle size range, the particle detector unable to directly detect the particles as being specific to particulate contamination or water contamination; and an electronic control system in communication with the particle detector, wherein the electronic control system is configured to:

determine, based on the raw particle counts for each of the plurality of predetermined particle size ranges, a first particle count of a first set of the particles in the first predetermined particle size range and a second particle count of a second set of the particles in the second predetermined particle size range, the first set of the particles non-overlapping with the second set of the particles;

determine a particle ratio of the first particle count and the second particle count;

determine whether the particle ratio exceeds a particle threshold indicative of an amount of water relative to particulate per unit volume of fuel;

in response to a determination of a dominant presence of water per unit volume of fuel, determine a total volume of water contamination based on the first particle count and the second particle count;

determine whether the total volume of water contamination exceeds a water threshold requiring at least one corrective action; and in response to a determination that the total volume of water contamination exceeds the water threshold, automatically initiate the at least one corrective action.

2. The fuel dispensing apparatus of claim 1, wherein the plurality of predetermined particle size ranges include a third predetermined particle size range.

3. The fuel dispensing apparatus of claim 2, wherein the plurality of predetermined particle size ranges include a fourth predetermined particle size range, the fourth predetermined particle size range being >21 µm.

4. The fuel dispensing apparatus of claim 2, wherein the first predetermined particle size range is >4 µm, the second predetermined particle size range is >6 µm, and the third predetermined particle size range is >14 µm.

5. The fuel dispensing apparatus of claim 2, wherein the first set of the particles is >4 µm and <6 µm, and the second set of the particles is >14 µm.

6. The fuel dispensing apparatus of claim 2, wherein the particle ratio is the second set of the particles >14 µm to the first set of the particles >4 µm and <6 µm.

7. The fuel dispensing apparatus of claim 1, wherein the electronic control system is configured to determine a dominant presence of water per unit volume of fuel if the particle ratio exceeds 40.

8. The fuel dispensing apparatus of claim 7, wherein the electronic control system is configured to determine a dominant presence of water per unit volume of fuel if the particle ratio exceeds 10.

9. The fuel dispensing apparatus of claim 1, wherein the electronic control system is configured to determine a dominant presence of particulate per unit volume of fuel if the particle ratio is less than 6.

10. The fuel dispensing apparatus of claim 9, wherein the electronic control system is configured to determine a dominant presence of particulate per unit volume of fuel if the particle ratio is less than 5.

11. The fuel dispensing apparatus of claim 1, wherein the electronic control system is further configured to receive ISO codes from the particle detector, the ISO codes comprising the raw particle counts for each of the plurality of predetermined particle size ranges.

12. The fuel dispensing apparatus of claim 11, wherein the ISO codes are ISO 4406 codes.

13. The fuel dispensing apparatus of claim 1, wherein the particle ratio comprises a first total volume of the first set of the particles in the first predetermined particle size range based on the first particle count to a second total volume of the second set of the particles in the second predetermined particle size range based on the second particle count.

14. The fuel dispensing apparatus of claim 1, wherein determining the particle ratio further comprises determining a total volume of particles in each of the plurality of predetermined particle size ranges per unit volume of fuel based on (i) a number of particles in each of the plurality of predetermined particle size ranges and (ii) predetermined empirical volume constants, each of the predetermined empirical volume constants representing an approximation of an average volume of particles in a respective one of the plurality of predetermined particle size ranges.

15. The fuel dispensing apparatus of claim 1, wherein the particle ratio comprises a first total mass of the first set of the particles in the first predetermined particle size range based on the first particle count to a second total mass of the second set of the particles in the second predetermined particle size range based on the second particle count.

16. The fuel dispensing apparatus of claim 1, wherein determining the particle ratio further comprises determining a total mass of particles in each of the plurality of predetermined particle size ranges based on (i) a number of particles in each of the plurality of predetermined particle size ranges and (ii) predetermined empirical mass constants.

17. The fuel dispensing apparatus of claim 1, wherein the at least one corrective action comprises generating a warning condition.

18. The fuel dispensing apparatus of claim 1, wherein the at least one corrective action comprises automatically reducing or preventing flow of fuel through the flow conduit.

19. The fuel dispensing apparatus of claim 18,
further comprising a differential pressure sensor configured to measure a pressure differential between a fuel input and a fuel output of a fuel filter,
wherein the electronic control system is configured to:
receive differential pressure information corresponding to the pressure differential from the differential pressure sensor in real time; and
determining whether to initiate the at least one corrective action based on the differential pressure information.

20. The fuel dispensing apparatus of claim 1, wherein determining the total volume of water contamination is based on particle counts in each of the plurality of predetermined particle size ranges.

21. A method of dispensing fuel comprising:
detecting, by a particle detector, particles in the fuel;
generating, by the particle detector, raw particle counts for each of a plurality of predetermined particle size ranges in real time as the fuel passes through a flow conduit, the plurality of predetermined particle size ranges comprising a first predetermined particle size range and a second predetermined particle size range, the particle detector unable to directly detect the particles as being specific to particulate contamination or water contamination;

determining, by an electronic control system in communication with the particle detector, based on the raw particle counts for each of the plurality of predetermined particle size ranges, a first particle count of a first set of the particles in the first predetermined particle size range and a second particle count of a second set of the particles in the second predetermined particle size range, the first set of the particles non-overlapping with the second set of the particles;

determining, by the electronic control system, a particle ratio of the first particle count to the second particle count;

determining, by the electronic control system, whether the particle ratio exceeds a particle threshold indicative of an amount of water relative to particulate per unit volume of fuel;

in response to a determination of a dominant presence of water per unit volume of fuel, determining, by the electronic control system, a total volume of water contamination based on the first particle count and the second particle count;

determining, by the electronic control system, whether the total volume of water contamination exceeds a water threshold requiring at least one corrective action; and in response to a determination that the total volume of water contamination exceeds the water threshold, automatically initiating, by the electronic control system, the at least one corrective action.

22. The method of claim 21, wherein determining the total volume of water contamination is based on particle counts in each of the plurality of predetermined particle size ranges.

* * * * *